US012232773B2

United States Patent
Mullaney

(10) Patent No.: US 12,232,773 B2
(45) Date of Patent: Feb. 25, 2025

(54) ADJUSTABLE RAIL APPARATUS FOR EXTERNAL FIXATION SYSTEMS

(71) Applicant: ARTHREX, INC., Naples, FL (US)

(72) Inventor: Michael W. Mullaney, Naples, FL (US)

(73) Assignee: ARTHREX, INC., Naples, FL (US)

( * ) Notice: Subject to any disclaimer, the term of this patent is extended or adjusted under 35 U.S.C. 154(b) by 1030 days.

(21) Appl. No.: 17/190,803

(22) Filed: Mar. 3, 2021

(65) Prior Publication Data

US 2021/0186562 A1 Jun. 24, 2021

Related U.S. Application Data

(63) Continuation of application No. PCT/US2019/049828, filed on Sep. 5, 2019.
(Continued)

(51) Int. Cl.
*A61B 17/64* (2006.01)
*A61B 17/66* (2006.01)

(52) U.S. Cl.
CPC .......... *A61B 17/6458* (2013.01); *A61B 17/66* (2013.01)

(58) Field of Classification Search
CPC ............................ A61B 17/6458; A61B 17/66
(Continued)

(56) References Cited

U.S. PATENT DOCUMENTS 5,405,347 A * 4/1995 Lee .................... A61B 17/6416
403/53
5,803,924 A 9/1998 Oni et al.
(Continued)

FOREIGN PATENT DOCUMENTS

CN 106725783 5/2017
EP 0944361 9/1999
(Continued)

OTHER PUBLICATIONS

International Search Report and Written Opinion of the International Searching Authority for International Application No. PCT/US2019/049828 mailed on Nov. 25, 2019.
(Continued)

*Primary Examiner* — Tessa M Matthews
*Assistant Examiner* — David C Comstock
(74) *Attorney, Agent, or Firm* — Carlson, Gaskey & Olds, P.C.

(57) ABSTRACT

Adjustable rail apparatuses and external bone and/or tissue fixation system including an adjustable rail apparatus is disclosed. The rail apparatuses comprise first and second external fixation beam elements with alignment grooves, and a joint coupling the first and second beam elements and configured to selectively adjust the relative angular and rotational arrangement of the first and second beam elements. The joint also comprises a first and second beam end housings rotationally fixed to the first and second external fixation beam elements, respectively. The joint also comprises first and second clamp members axially and rotationally fixed to the first and beam end housings, respectively. The joint also comprises first and second rotation end housings coupled with the first and second clamp members, respectively, the first and second rotation end housings being selectively rotatably adjusted with respect to the first and second clamp members, respectively, within fixed ranges of rotation.

31 Claims, 23 Drawing Sheets

Related U.S. Application Data

(60) Provisional application No. 62/727,116, filed on Sep. 5, 2018.

(58) Field of Classification Search
USPC ....... 606/54, 57, 58, 59, 256, 258, 259, 260; 403/43, 46, 48, 53, 59, 60, 63, 72, 73, 75, 403/78, 79, 83, 84, 110, 118, 152, 154, 403/157, 196, 287
See application file for complete search history.

(56) References Cited

U.S. PATENT DOCUMENTS

| | | | |
|---|---|---|---|
| 5,902,302 A | 5/1999 | Berki et al. | |
| 5,941,877 A | 8/1999 | Viegas et al. | |
| 6,019,769 A | 2/2000 | McCarthy et al. | |
| 9,867,637 B2 | 1/2018 | Sanders et al. | |
| 2006/0229602 A1 | 10/2006 | Olsen | |
| 2007/0038217 A1 * | 2/2007 | Brown | A61B 17/6466 606/57 |

FOREIGN PATENT DOCUMENTS

| | | | | |
|---|---|---|---|---|
| EP | 1844721 A1 * | 10/2007 | ......... | A61B 17/6416 |
| GB | 2519981 A | 5/2015 | | |
| JP | H11513594 A | 11/2006 | | |
| JP | 2016503708 A | 2/2016 | | |
| WO | 2017151822 | 9/2017 | | |

OTHER PUBLICATIONS

Extended European Search Report issued in European Patent Application No. 19856630.9, May 11, 2022, 11 pages.

Notice of Reasons for Rejection for Japanese Patent Application No. 2021-512636 mailed Mar. 5, 2024.

International Preliminary Report on Patentability for International Application No. PCT/US2019/049828, Mar. 9, 2021, 8 pages, International Bureau of WIPO.

* cited by examiner

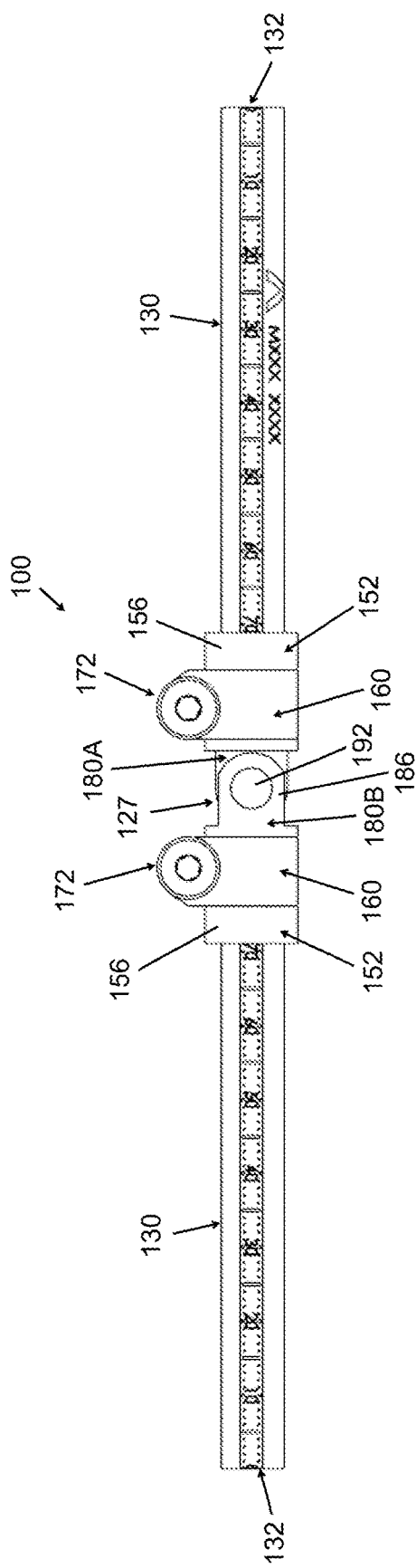
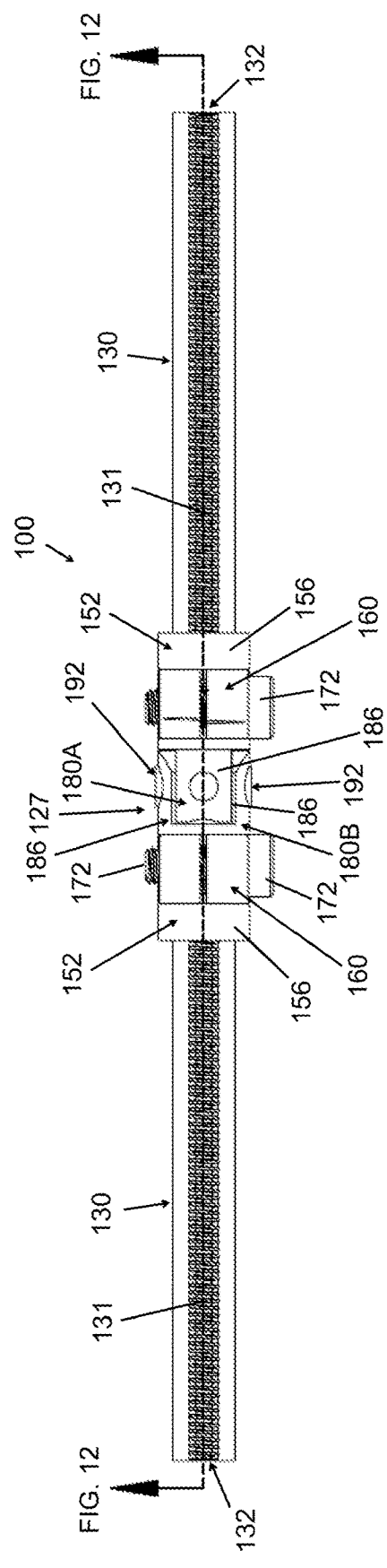

ADJUSTABLE RAIL APPARATUS FOR EXTERNAL FIXATION SYSTEMS

CROSS-REFERENCE TO RELATED APPLICATIONS

This application claims priority benefit from International Application No. PCT/US2019/049828 filed on Sep. 5, 2019, which claimed priority from U.S. Provisional Application No. 62/727,116 filed Sep. 5, 2018, each of which is incorporated herein by reference in its entirety.

FIELD OF THE INVENTION

The present disclosure is generally directed to rails for external bone fixation systems and related methods. More particularly, the present disclosure is directed to adjustable rails for external bone fixation systems and related methods that allow adjustability between the orientation between two or more rail portions.

BACKGROUND OF THE INVENTION

External fixation devices have been used to treat bone and tissue conditions by positioning bone or tissue segments in desired relative positions based on particular clinical needs. One form of external fixation devices is a unilateral or mono-lateral rail based fixation device. These devices are typically comprised of a rail or beam element serving as the structural backbone of the device, along which are slidably attached clamp assemblies that can accept fixation elements such as bone fixation pins or wires. In some embodiments, these clamp assemblies have the ability to be statically locked to the rail, or be dynamically driven or translated axially along the rail. In some embodiments, the clamp assemblies can be rotated about the rail and/or angulated relative to the axis of the rail.

When configured as bone or tissue fixation systems, some external fixation systems typically include a multitude of clamp assemblies. In the most basic configurations, there is one static clamp assembly and one drivable clamp assembly coupled to the beam element. In some embodiments, the beam element and the clamp assemblies arranged in this way can be connected to a second beam and clamp assembly through the use of a joint element having one or more degrees of freedom, such as a hinge having one degree of freedom to a spherical or cardan joint having three degrees of freedom. However, the beam element itself is typically linear and static (i.e., is not adjustable out of the linear shape or pathway). The relative positioning and orientation between two or more clamps coupled to the rail is thereby limited by the linear nature of the rail. Further, adding or removing parts of the clamp assemblies and/or additional segments or extensions to the rail to suit a particular anatomical or fixation arrangement can be cumbersome and/or time consuming.

External bone fixation rails and external bone fixation systems with rails that provide with two or more rail segments and a joint that can be selectively adjusted to adjust the orientation between the rail segments to facilitate optimal fixation of bone elements via clamps coupled to the rail segments (and thereby corresponding bones or bone segments) is therefore desirable.

SUMMARY OF THE INVENTION

In one aspect, the present disclosure provides external fixation systems comprised of a longitudinal rail or beam apparatus that accepts and guides a multitude of clamp assemblies (of the same or differing configuration) positionable in differing positions and/or orientations relative to the rail. The rail apparatus may include a plurality of rail segments with an adjustable joint coupling and extending between adjacent segments. The rail segments may include an axial engagement feature, such as a threaded or ribbed track, that extends along the length or axis of the rail segments that serves as a point of driving engagement for each of the clamp assemblies. The engagement feature is configured to allow the clamp assemblies to be locked in place along the axis or length of the respective rail segments, and to be selectively driven or translated along the respective rail segments. Each rail segment may also include an axially extending alignment groove, and a central bore of the least one drivable fixation clamp assembly includes an anti-rotation member that extends into the alignment groove to rotationally fix the least one drivable fixation clamp assembly and a beam segment/element about the axis of the beam segment.

In another aspect, the present disclosure provides a joint apparatus for coupling and selectively adjusting the relative angular and rotational arrangement of first and second external fixation beam elements. The apparatus comprises a first beam end housing comprising a sleeve portion configured to rotationally fix to the first external fixation beam element and a post portion; a first screw configured to axially fix the first beam end housing to the first external fixation beam element; a first clamp member axially and rotationally fixed to the post portion of the first external fixation beam element; and a first rotation end housing comprising a rotation portion and a post portion coupled with the first clamp member, the first rotation end housing being selectively rotatably adjusted with respect to the first clamp member within a fixed range of rotation. The apparatus further comprises a second beam end housing comprising a sleeve portion configured to rotationally fix to the second external fixation beam element and a post portion; a second screw configured to axially fix the second beam end housing to the second external fixation beam element; a second clamp member axially and rotationally fixed to the post portion of the second external fixation beam element; and a second rotation end housing comprising a rotation portion and a post portion coupled with the second clamp member, the second rotation end housing being selectively rotatably adjusted with respect to the second clamp member within a fixed range of rotation. The rotation portions of the first and second rotation end housings are rotationally coupled about an axis of rotation. The first clamp member comprises a compression screw configured to selectively apply a compressive force to selectively rotatably fix the first rotation end housing to the first clamp member, and the second clamp member comprises a compression screw configured to selectively apply a compressive force to selectively rotatably fix the second rotation end housing to the second clamp member.

In some embodiments, the first beam end housing, the first clamp member and the first rotation end housing comprise apertures that form a passageway extending from the rotation portion of the first rotation end housing to the first screw. In some embodiments, the first beam end housing, the first clamp member, the first rotation end housing and the second rotation end housing comprise apertures that form a passageway extending from the rotation portion of the first rotation end housing to the second screw in a first relative orientation of the first and second rotation end housings about the axis of rotation. In some embodiments, the axis of rotation intersects axes of the first and second screws. In some embodiments, the axis of rotation is oriented perpendicular to axes of the first and second screws.

In another aspect, the present disclosure provides an adjustable rail apparatus comprising a first elongate external fixation element defining a first axis and comprising a first axially extending threaded track portion; a second elongate external fixation element defining a second axis and comprising a second axially extending threaded track portion; and a joint apparatus disclosed herein coupling the first and second elongate external fixation beam elements.

In some embodiments, the axis of rotation intersects axes of the first and second elongate external fixation elements. In some embodiments, the axis of rotation is oriented perpendicular to axes of the first and second elongate external fixation elements.

In another aspect, the present disclosure provides an external bone and/or tissue fixation system, comprising an adjustable rail apparatus disclosed herein; and at least one drivable fixation clamp assembly coupled to one of the first and second elongate external fixation beam elements.

In another aspect, the present disclosure provides an adjustable rail apparatus. The adjustable rail apparatus comprises an elongate first external fixation beam element comprising a first axis and an external surface with an alignment groove, an elongate external fixation beam element comprising a second axis, an external surface with an alignment groove, and a joint coupling the first and second beam elements and configured to selectively adjust the relative angular and rotational arrangement of the first and second beam elements. The joint comprises a first beam end housing comprising a post portion and sleeve portion rotationally fixed to the first external fixation beam element, a first screw axially fixing the first beam end housing to the first external fixation beam element, a first clamp member axially and rotationally fixed to the post portion of the first beam end housing, and a first rotation end housing comprising a rotation portion and a post portion coupled with the first clamp member, the first rotation end housing being selectively rotatably adjusted with respect to the first clamp member within a fixed range of rotation. The joint also comprises a second beam end housing comprising a post portion and sleeve portion rotationally fixed to the second external fixation beam element, a second screw axially fixing the second beam end housing to the second external fixation beam element, a second clamp member axially and rotationally fixed to the post portion of the second beam end housing, and a second rotation end housing comprising a rotation portion and a post portion coupled with the second clamp member, the second rotation end housing being selectively rotatably adjusted with respect to the second clamp member within a fixed range of rotation. The rotation portions of the first and second rotation end housings are rotationally fixed and pivotably angularly coupled about a third axis that is angled with respect to the first and second axes of the first and second external fixation beam elements, respectively. The first clamp member comprises a first compression screw configured to selectively apply a compressive force to the post portion of the first rotation end housing to selectively rotatably and axially fix the first clamp member and the first rotation end housing. The second clamp member comprises a second compression screw configured to selectively apply a compressive force to the post portion of the second rotation end housing to selectively rotatably and axially fix the second clamp member and the second rotation end housing.

In some embodiments, the first beam end housing, the first clamp member and the first rotation end housing comprise first apertures that form a first passageway extending from the rotation portion of the first rotation end housing to the first screw. In some embodiments, the first beam end housing, the first clamp member, the first rotation end housing and the second rotation end housing comprise second apertures that form a second passageway extending from the rotation portion of the first rotation end housing to the second screw in a first relative orientation of the first and second rotation end housings about the axis of rotation.

In some embodiments, the third axis intersects the first and second axes. In some embodiments, the third axis is oriented perpendicular to the first and second axes.

In some embodiments, a first end portion of the first external fixation beam element is positioned within an opening of the sleeve portion of the first beam end housing, and the joint further comprises a first pin member coupled to the sleeve portion and including a portion extending within the opening of the sleeve portion and along a portion of the alignment groove of the first external fixation beam element to rotationally fix to the first beam end housing and the first external fixation beam element. In some such embodiments, the first end portion of the first beam element includes an internally threaded axial aperture, the first beam end housing includes an axial aperture extending through the post portion thereof to the opening of the sleeve portion thereof, and the first screw comprises an externally threaded shaft portion that is threadably coupled within the internally threaded axial aperture of the first end portion of the first beam element. In some such embodiments, the first screw further comprises a head portion that defines a cross-sectional size that is larger than that of a portion of the axial aperture of the first beam end housing such that the head portion is prevented from axially passing therethrough to axially fix the first beam end housing and the first external fixation beam element.

In some embodiments, the first clamp member comprises an internally threaded bore comprising a first end portion that is threadably coupled with the post portion of the first beam end housing and includes a first slot comprising a width that corresponds to a width of the first pin member, and the first pin member further includes a portion extending axially along an outer side of the post portion of the first beam end housing and within the first slot of the threaded bore of the first clamp member to rotationally and axially fix the first clamp member and the first beam end housing. In some such embodiments, the internally threaded bore of the first clamp member further comprises a second end portion that is threadably coupled with the post portion of the first rotation end housing and includes a first non-threaded recessed portion comprising a width that is wider than a width of a second pin member that is coupled to the first rotation end housing, and the second pin member includes a portion extending axially along an outer side of the post portion of the first rotation end housing and within the first non-threaded recessed portion of the threaded bore of the first clamp member to selectively allow a limited range of relative rotation between the first clamp member and the first rotation end housing. In some such embodiments, the first clamp member comprises a compression slot that extends from an outer side thereof to the internally threaded bore along an entire axial length of the first clamp member and a pair of first clamping portions with substantially aligned clamping apertures on opposing sides of the compression slot, and the joint further comprises a first compression screw that extends within the clamping apertures of the first clamping portions and is threadably coupled with at least one of the clamping apertures of the first clamping portions such that rotation of the first clamping screw about an axis thereof in a first direction draws the first clamping portions towards each other and deforms the internally threaded bore of the first clamp member inwardly such that the first clamp member exerts a compressive force on the post portion of the first rotation end housing to selectively rotatably fix the first clamp member and the first rotation end housing, and rotation of the first clamping screw about the axis thereof in a second direction that opposes the first direction allows the internally threaded bore of the first clamp member to deform outwardly such that the first clamp member exerts less compressive force or no compressive force on the post portion of the first rotation end housing to selectively allow the limited range of relative rotation between the first clamp member and the first rotation end housing. In some such embodiments, the rotation portions of the first and second rotation end housings are pivotably coupled via a joint pin that defines the third axis. In some such embodiments, the first and second rotation end housings comprise a split flange yoke and a shaft portion that are pivotably coupled via the joint pin, the shaft portion being positioned within the split flange yoke.

In some embodiments, the rotation portions of the first and second rotation end housings are pivotably coupled via a joint pin that defines the third axis. In some such embodiments, the rotation portions of the first and second rotation end housings comprise a split flange yoke and a shaft portion that are pivotably coupled via the joint pin, the shaft portion being positioned within the split flange yoke.

In some embodiments, a second end portion of the second external fixation beam element is positioned within an opening of the sleeve portion of the second beam end housing, and the joint further comprises a third pin member coupled to the sleeve portion and including a portion extending within the opening of the sleeve portion and along a portion of the alignment groove of the second external fixation beam element to rotationally fix to the second beam end housing and the second external fixation beam element. In some such embodiments, the second end portion of the second beam element includes an internally threaded axial aperture, the second beam end housing includes an axial aperture extending through the post portion thereof to the opening of the sleeve portion thereof, and the second screw comprises an externally threaded shaft portion that is threadably coupled within the internally threaded axial aperture of the second end portion of the second beam element. In some such embodiments, the second screw further comprises a head portion that defines a cross-sectional size that is larger than that of a portion of the axial aperture of the second beam end housing such that the head portion is prevented from axially passing therethrough to axially fix the second beam end housing and the second external fixation beam element. In some such embodiments, the second clamp member comprises an internally threaded bore comprising a first end portion that is threadably coupled with the post portion of the second beam end housing and includes a second slot comprising a width that corresponds to a width of the third pin member, and the third pin member further includes a portion extending axially along an outer side of the post portion of the second beam end housing and within the first slot of the threaded bore of the second clamp member to rotationally and axially fix the second clamp member and the second beam end housing. In some such embodiments, the internally threaded bore of the second clamp member further comprises a second end portion that is threadably coupled with the post portion of the second rotation end housing and includes a second non-threaded recessed portion comprising a width that is wider than a width of a fourth pin member that is coupled to the second rotation end housing, and the fourth pin member includes a portion extending axially along an outer side of the post portion of the second rotation end housing and within the second non-threaded recessed portion of the threaded bore of the second clamp member to selectively allow a limited range of relative rotation between the second clamp member and the second rotation end housing. In some such embodiments, the second clamp member comprises a compression slot that extends from an outer side thereon to the internally threaded bore along an entire axial length of the second clamp member and a pair of second clamping portions with substantially aligned clamping apertures on opposing sides of the compression slot, and the joint further comprises a second compression screw that extends within the clamping apertures of the second clamping portions and is threadably coupled with at least one of the clamping apertures of the second clamping portions such that rotation of the second clamping screw about an axis thereof in a first direction draws the second clamping portions towards each other and deforms the internally threaded bore of the second clamp member inwardly such that the second clamp member exerts a compressive force on the post portion of the second rotation end housing to selectively rotatably fix the second clamp member and the second rotation end housing, and rotation of the second clamping screw about the axis thereof in a second direction that opposes the first direction allows the internally threaded bore of the second clamp member to deform outwardly such that the second clamp member exerts less compressive force or no compressive force on the post portion of the second rotation end housing to selectively allow the limited range of relative rotation between the second clamp member and the second rotation end housing. In some such embodiments, the first clamp member comprises an internally threaded bore comprising a first end portion that is threadably coupled with the post portion of the first beam end housing and includes a first slot comprising a width that corresponds to a width of the first pin member, and the first pin member further includes a portion extending axially along an outer side of the post portion of the first beam end housing and within the first slot of the threaded bore of the first clamp member to rotationally and axially fix the first clamp member and the first beam end housing. In some such embodiments, the internally threaded bore of the first clamp member further comprises a second end portion that is threadably coupled with the post portion of the first rotation end housing and includes a first non-threaded recessed portion comprising a width that is wider than a width of a second pin member that is coupled to the first rotation end housing, and the second pin member includes a portion extending axially along an outer side of the post portion of the first rotation end housing and within the first non-threaded recessed portion of the threaded bore of the first clamp member to selectively allow a limited range of relative rotation between the first clamp member and the first rotation end housing. In some such embodiments, the first clamp member comprises a compression slot that extends from an outer side thereon to the internally threaded bore along an entire axial length of the first clamp member and a pair of first clamping portions with substantially aligned clamping apertures on opposing sides of the compression slot, and the joint further comprises a first compression screw that extends within the clamping apertures of the first clamping portions and is threadably coupled with at least one of the clamping apertures of the first clamping portions such that rotation of the first clamping screw about an axis thereof in a first direction draws the first clamping portions towards each other and deforms the internally threaded bore of the first clamp member inwardly such that the first clamp member exerts a compressive force on the post portion of the first rotation end housing to selectively rotatably fix the first clamp member and the first rotation end housing, and rotation of the first clamping screw about the axis thereof in a second direction that opposes the first direction allows the internally threaded bore of the first clamp member to deform outwardly such that the first clamp member exerts less compressive force or no compressive force on the post portion of the first rotation end housing to selectively allow the limited range of relative rotation between the first clamp member and the first rotation end housing.

In another aspect, the present disclosure provides an external bone and/or tissue fixation system. The fixation system comprise an adjustable rail apparatus as described above, and at least one drivable fixation clamp assembly coupled to one of the first and second first external fixation beam element.

In some embodiments, the at least one drivable fixation clamp assembly is configured to axially translate along the one of the first and second first external fixation beam elements via an axial-extending track portion of the exterior surface thereof. In some such embodiments, the axial-extending track portion comprises an externally threaded or patterned engagement track. In some embodiments, the at least one drivable fixation clamp assembly is rotationally fixed to the one of the first and second first external fixation beam elements via the alignment groove thereof.

These and other objects, features and advantages of this disclosure will become apparent from the following detailed description of the various aspects of the disclosure taken in conjunction with the accompanying drawings.

BRIEF DESCRIPTION OF THE DRAWINGS

For the purposes of illustrating the adjustable rails, external bone and/or tissue fixation systems and related fixation methods described herein, illustrative embodiments are provided. These illustrative embodiments are in no way limiting in terms of the precise configuration, arrangement and operation of the disclosed adjustable rails, external bone and/or tissue fixation systems and related fixation methods, and other similar embodiments are envisioned.

FIG. 10 illustrates another side elevational view of the exemplary adjustable rail apparatus of FIG. 6 in a linear arrangement, in accordance with the present disclosure;

FIG. 11 illustrates a top view of the exemplary adjustable rail apparatus of FIG. 6 in a linear arrangement, in accordance with the present disclosure;

DETAILED DESCRIPTION

Figure 1:
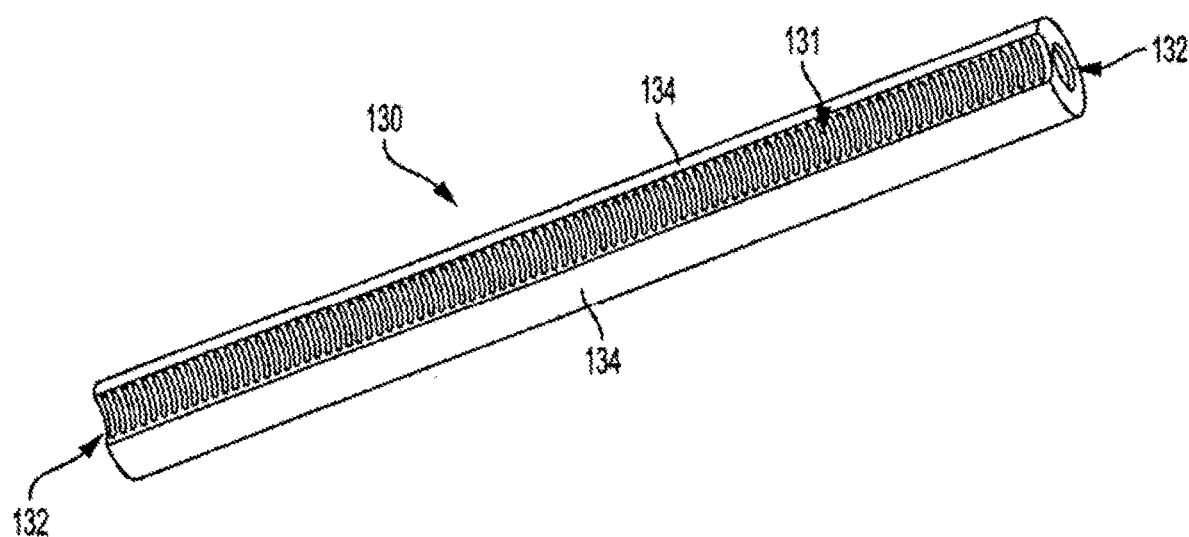
FIG. 1 illustrates a perspective view of an exemplary beam element of an external fixation system, in accordance with the present disclosure.
Figure 2:
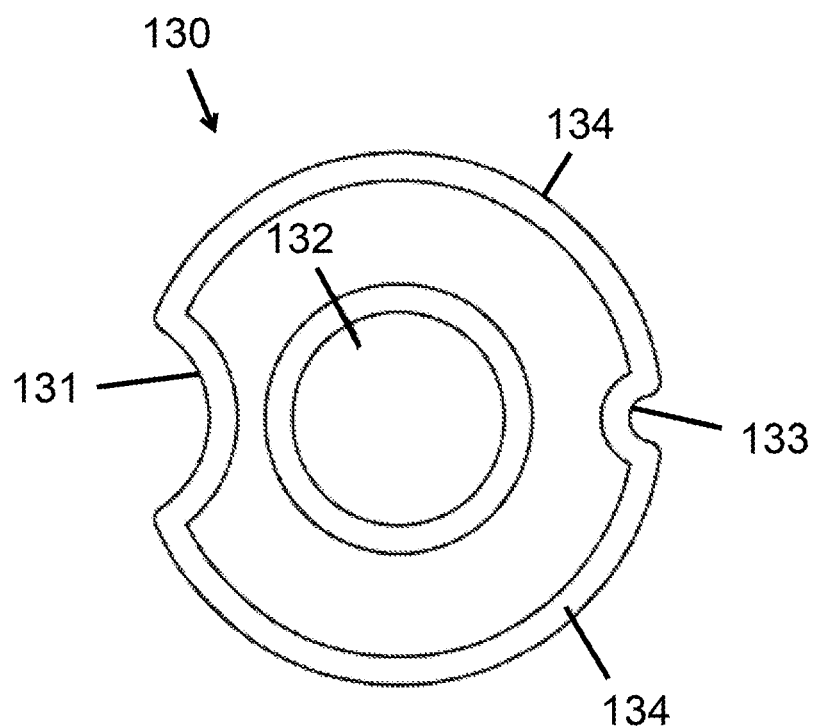
FIG. 2 illustrates an end view of the exemplary beam element of FIG. 1, in accordance with the present disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Any examples of parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

The present disclosure provides for external bone or tissue fixation systems and related fixation methods 100, as shown in FIGS. 6-26. The fixation systems and methods 100 include one or more independently drivable clamp assembly (not shown) (which may provide at least 3DOF) that are each translatable or drivable along rail segments 132A, 132B . . . 132N of a rail apparatus 130. In some other embodiments (not shown), the fixation systems and methods 100 may include at least one fixed rotatable end clamp assembly (which may provide at least 2DOF) positioned at a free end of one of the rail segments 132A, 132B . . . 132N. The fixation systems and methods 100 of FIGS. 6-26 may be configured or particularly advantageous for use with relatively small bones, such as bones of a hand or foot. For example, the fixation systems and methods 100 of FIGS. 6-26 may be configured or particularly advantageous to fix two or more small bones or bone segments of one or more relatively small bone with respect to each other, such one or more bones or bone segments of a hand or foot. In some embodiments, the fixation systems and related fixation methods 100, as shown in FIGS. 6-26, may be configured or particularly advantageous for the repair of fractures or deformities of one or more bone, such as fractures of or deformities in one or more relatively small bone in a hand or foot. However, the fixation systems and related fixation methods 100 may also be configured or particularly advantageous to fix two or more relatively long bones or bone segments of one or more relatively long bone with respect to each other, such one or more bones or bone segments of an arm or leg.

The present application thereby provides external bone fixation systems that provide for relative movement of two or more bones or bone segments with respect to each other. The systems may include movable and drivable clamp assemblies located along the axial length of rail elements 130 (with provisions to allow for the attachment of at least one non-traveling clamp assemblies 120), and the relative orientation between rail elements 130 may be adjustable or movable with respect to each other through the use of a joint mechanism 127, such as but not limited to a joint that provides for adjustment of the angle between the axes of the rail elements 130 and/or the orientation of the rail elements 130 about their axes, as shown in FIGS. 1-12.

As shown in FIGS. 1-12, the beam segments or elements 130 (to which at least one drivable clamp assemblies and/or at least one fixed clamp assembly can be coupled) may comprise axially-extended or axially elongate beams 130 that each define an axis or linear length along a first direction. At least one drivable clamp assembly may be translatably or drivably coupled to the exterior of each beam element 130, such as a plurality of drivable clamp assemblies 110 translatably coupled to the exterior of the beam elements 130 spaced along the axis or axial length of the beam elements 130. For example, an exemplary fixation system and method including at least a pair of beam elements 130 may be positioned into a first configuration with the main axes of the beam elements 130 (and thereby clamp assemblies coupled thereon) being aligned (e.g., co-linear and/or commonly oriented about their axes). From such a first configuration, the joint between the beam elements 130 may be adjusted such that pair of beam elements 130 are re-positioned into a second configuration with the main axes of the beam elements 130 (and thereby clamp assemblies coupled thereon) being offset for each other (e.g., the axes being angled with respect to each other and/or oriented differently about their axes).

As noted above, in some embodiments at least one drivable clamp assembly may pass over the beam elements 130. Stated differently, in some embodiments the beam elements 130 may extend through at least one drivable clamp assembly, and the at least one drivable clamp assembly may be configured to translate along or over the exterior surface of at least the respective beam element 130.

As shown in FIGS. 1-12, the beam elements 130 may be at least generally cylindrical and define an exterior surface that extends about the axis and between substantially opposing free ends (e.g., a generally cylindrical exterior surface with opposing bases or free ends). At least one end of the beam element 130 may include an aperture or hole 132 extending at least substantially axially into the beam element 130 from the end surface, as shown in FIGS. 1-12. The axially-extending aperture 132 may extend along the axial length of the beam element 130 at least partially into the interior or medial portion of the beam element 130 (along the axial direction). The at least one end aperture 132 of the beam element 130 may include internal threads such that the at least one end aperture 132 comprises a tapped hole 132. As shown in FIGS. 1-12, the at least one end aperture 132 may thereby be configured to threadably couple or mate with external threads of a bolt portion of an end clamp assembly. Similarly, the at least one end aperture 132 may thereby be configured to threadably couple or mate with external threads of another beam element 130 or hinge or connection mechanism (e.g., a dual threaded hinge or connection mechanism) to removably couple the ends of a pair of beam elements 130. The beam apparatus 100 may thereby be effectively axially lengthened via the additional beam element. In other embodiments, the beam element 130 and/or the at least one end aperture 132 of the beam element 130 may be non-threaded or include another configuration or mechanism besides internal threads for mating with a rotatable end clamp assembly 120 and/or an additional beam element.

As shown in FIGS. 1-12, the exterior surface of the beam elements 130 may be generally cylindrical and include an externally threaded or patterned engagement track 131 and an alignment groove or slot 133. The externally threaded or patterned engagement track 131 and/or the alignment groove 133 may extend along the axial length of the exterior surface of the beam element 130 for the entire length of the beam element 130 or partially along the length of the beam element 130. As shown in FIGS. 1-12, the engagement track 131 may be indented or recessed into the beam element 130.

In this way, the track 131 may form a groove extending radially into or within the beam element 130. The engagement track 131 may form a portion of the exterior surface of the beam element 130. In some embodiments, as shown in FIGS. 4-8, the engagement track 131 may be a groove defined by a radius. As shown in FIGS. 4-8, the track 131 may include external threads (or internal threads, depending upon perspective) or other surface features extending along the axial length of the track 131. The threads of the engagement track 131 may mate with threads of a driving member of a drivable clamp assembly to allow the drivable clamp assembly to be axially translated or driven along the length of the beam element 130 via a driving member. As such, the pitch of the threads of the engagement track 131 and the threads of the driving member of a drivable clamp assembly may have compatible pitches and/or other configurations. In some embodiments, the engagement track 131 may be a hemispherical threaded groove extending into the beam element 130. It is noted that such a radial or hemispherical grooved threaded engagement track 131 may be machined relatively easily. For example, the hemispherical grooved threaded engagement track 131 may be machined via ball end-mill which alleviates difficulties associated with tap a relatively long partial bore, such as opposed to a standard 60 thread or a trapezoidal thread for example. However, the engagement track 131 may include any thread design and/or other surface feature to allow a clam assembly to lock or fix to the beam element 130 and/or axially drive along the beam element 130.

As also shown in FIGS. 1-12, similar to the engagement track 131, the alignment groove 133 may be indented or recessed into the beam element 130. In this way, the alignment groove 133 may form a groove extending radially into or within the beam element 130. The alignment groove 133 may form a portion of the exterior surface of the beam element 130. In some embodiments, as shown in FIGS. 1-12, the alignment groove 133 may be defined by a radius, such as a hemispheric-al groove. In other embodiments, the alignment groove 133 may be any other shape or configuration. The alignment groove 133 may couple with an alignment member (such as a pin or ball bearing) of a drivable clamp assembly to allow the drivable clamp assembly 110 to be axially translated or driven along the length of the beam element 130 (via the driving member and engagement track 131) while being aligned or positioned in a particular orientation about the axis of the beam element 130, as explained further below. The alignment groove 133 may thereby serve as a linear, partially cylindrical groove that serves to provide anti-rotation of a drivable clamp assembly about the beam element 130, as explained further below. The alignment groove 133 and the drivable clamp assembly may mate via the alignment member only in a particular relative orientation between the drivable clamp assembly and the beam element 130, and may prevent the drivable clamp assembly from rotating about the beam element 130 from such an orientation (but allow the drivable clamp assembly to translate or slide axially along the alignment groove 133 when being axially driven via the driving member thereof.

In some embodiments, the beam element 130 may include intermediate exterior surface portions 134 extending between the alignment groove 133 and the engagement track 131 portions of the beam element 130, as shown in FIGS. 1-12. In some embodiments, the alignment groove 133 and the engagement track 131 portions of the beam element 130 may substantially oppose each other about the axis of the beam element 130, and thereby two substantially similar intermediate exterior surface portions 134 may extend therebetween. In other embodiments, the alignment groove 133 and the engagement track 131 portions of the beam element 130 may be offset about the axis of the beam element 131. As shown in FIGS. 1-12, the intermediate exterior surface portions 134 may be substantially smooth surfaces (e.g., non-threaded surfaces), and may be curved or arcuate. In some embodiments, the intermediate exterior surface portions 134 may be cylindrical surface portions extending about the axis of the beam element 130 (e.g., convex surfaces defined by a single radius) and/or along the axial length of the beam element 130.

Figure 3:
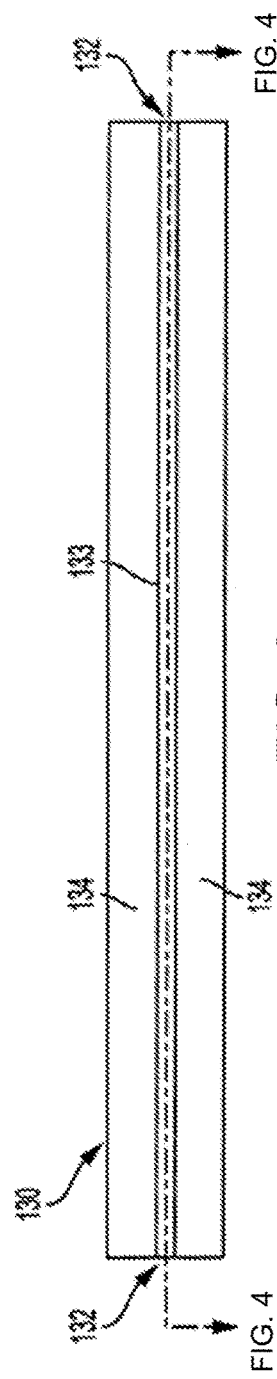
FIG. 3 illustrates a side view of the exemplary beam element of FIG. 1, in accordance with the present disclosure.
Figure 4:
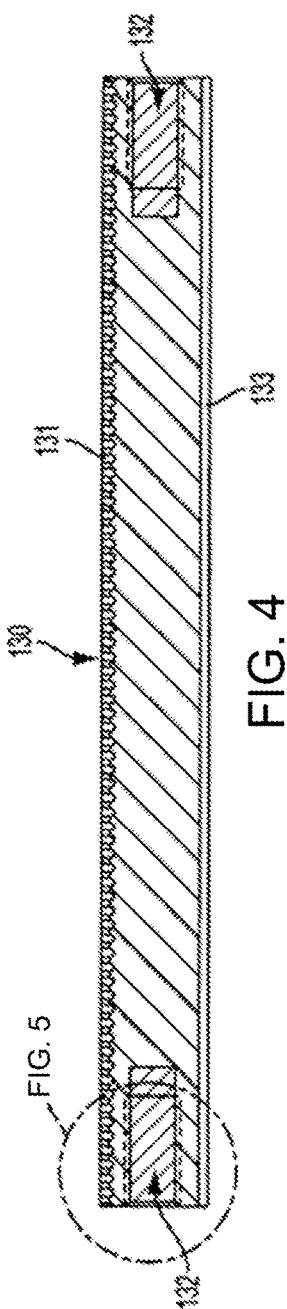
FIG. 4 illustrates a cross-sectional side view of the exemplary beam element of FIG. 1, along Line 4-4 of FIG. 3, in accordance with the present disclosure.
Figure 5:
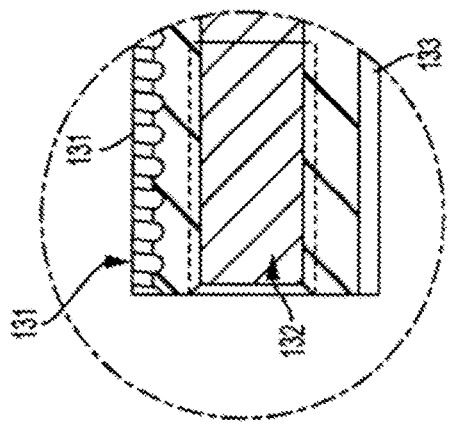
FIG. 5 illustrates an enlarged cross-sectional view of a portion of the exemplary beam element of FIG. 1 as indicted in FIG. 4, in accordance with the present disclosure.
Figure 6:
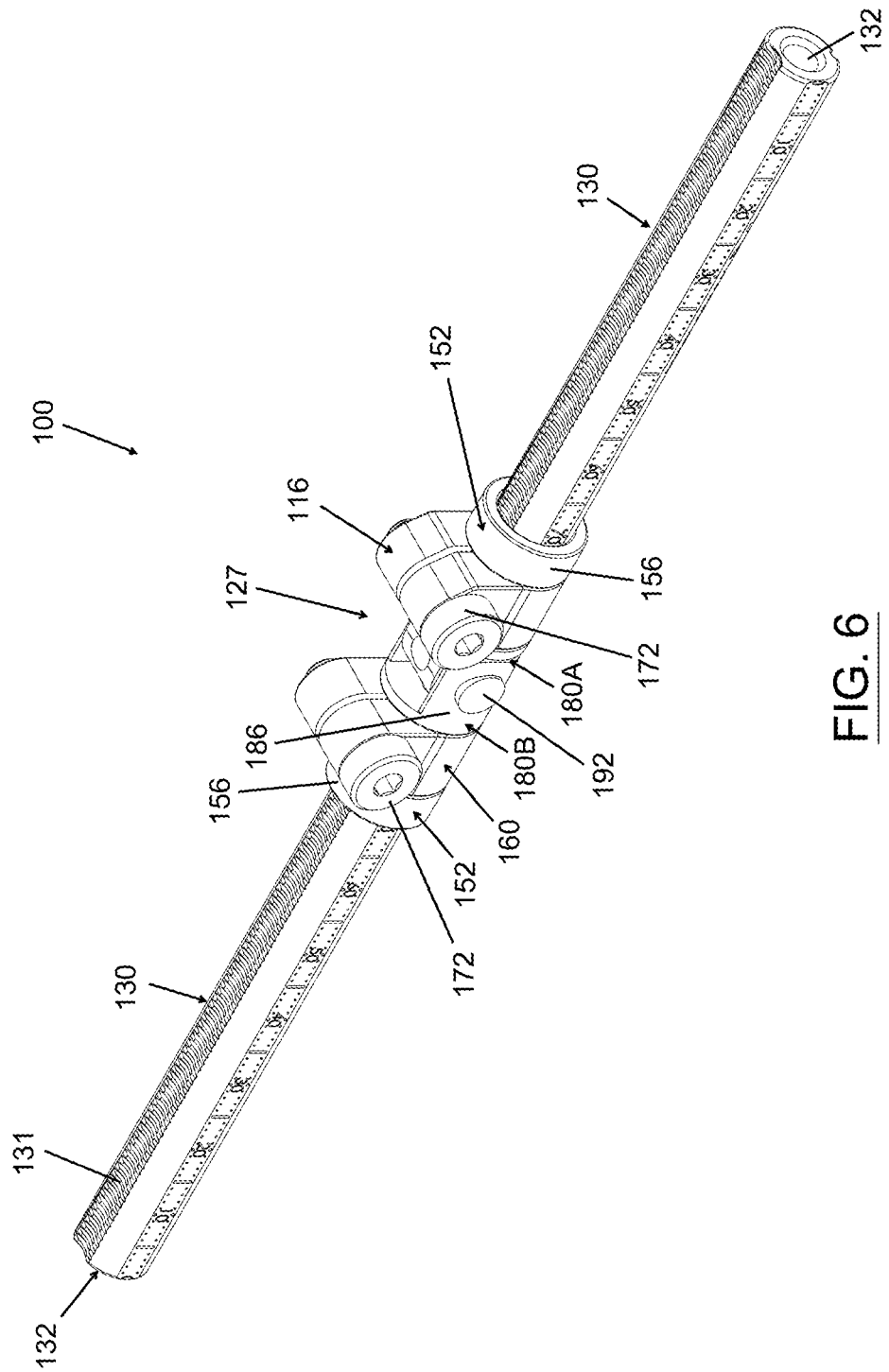
FIG. 6 illustrates an elevational perspective view of an adjustable rail apparatus for an external fixation system including a pair of the exemplary beam elements of FIGS. 1-5 coupled via an exemplary adjustable hinge in a linear arrangement, in accordance with the present disclosure.
Figure 7:
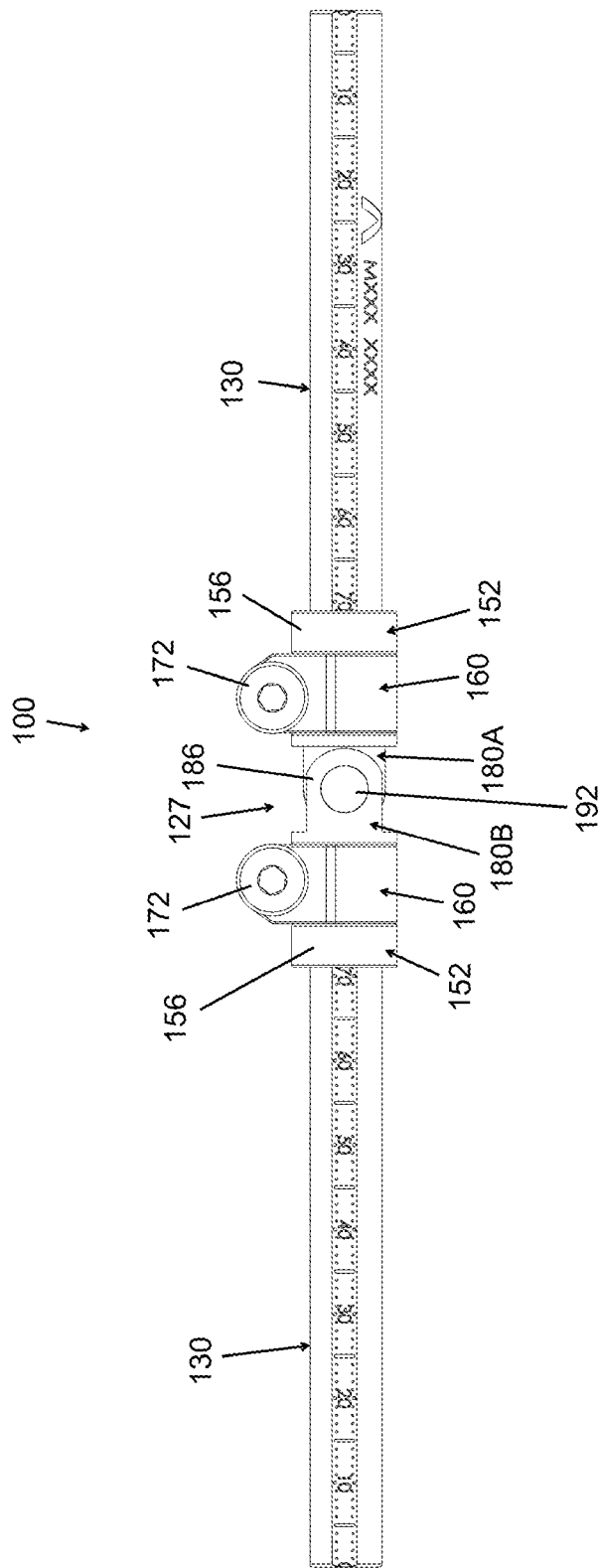
FIG. 7 illustrates a side elevational view of the exemplary adjustable rail apparatus of FIG. 6 in a linear arrangement, in accordance with the present disclosure.
Figure 8:
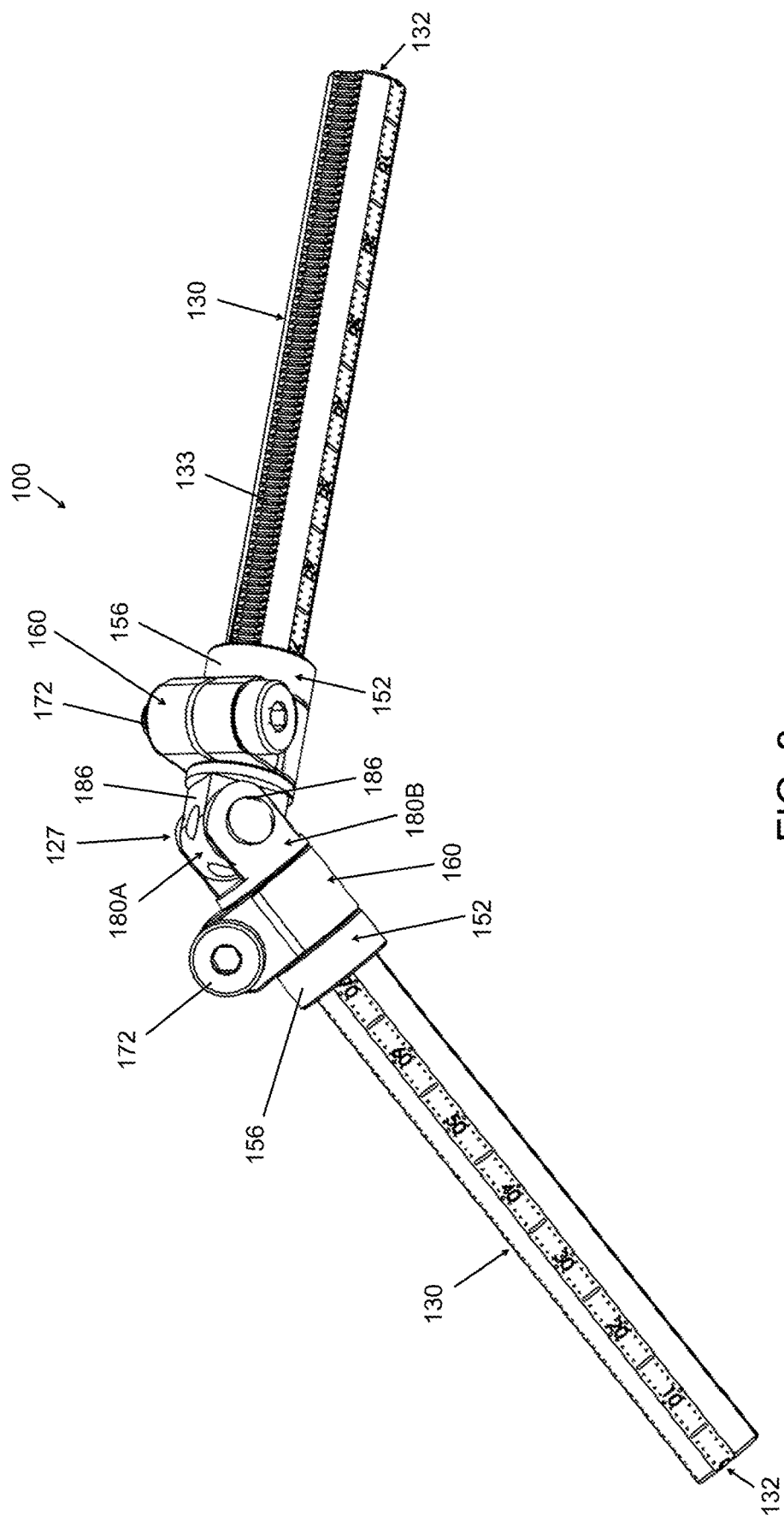
FIG. 8 illustrates an elevational perspective view of the exemplary adjustable rail apparatus of FIG. 6 in a non-linear arrangement, in accordance with the present disclosure.
Figure 9:
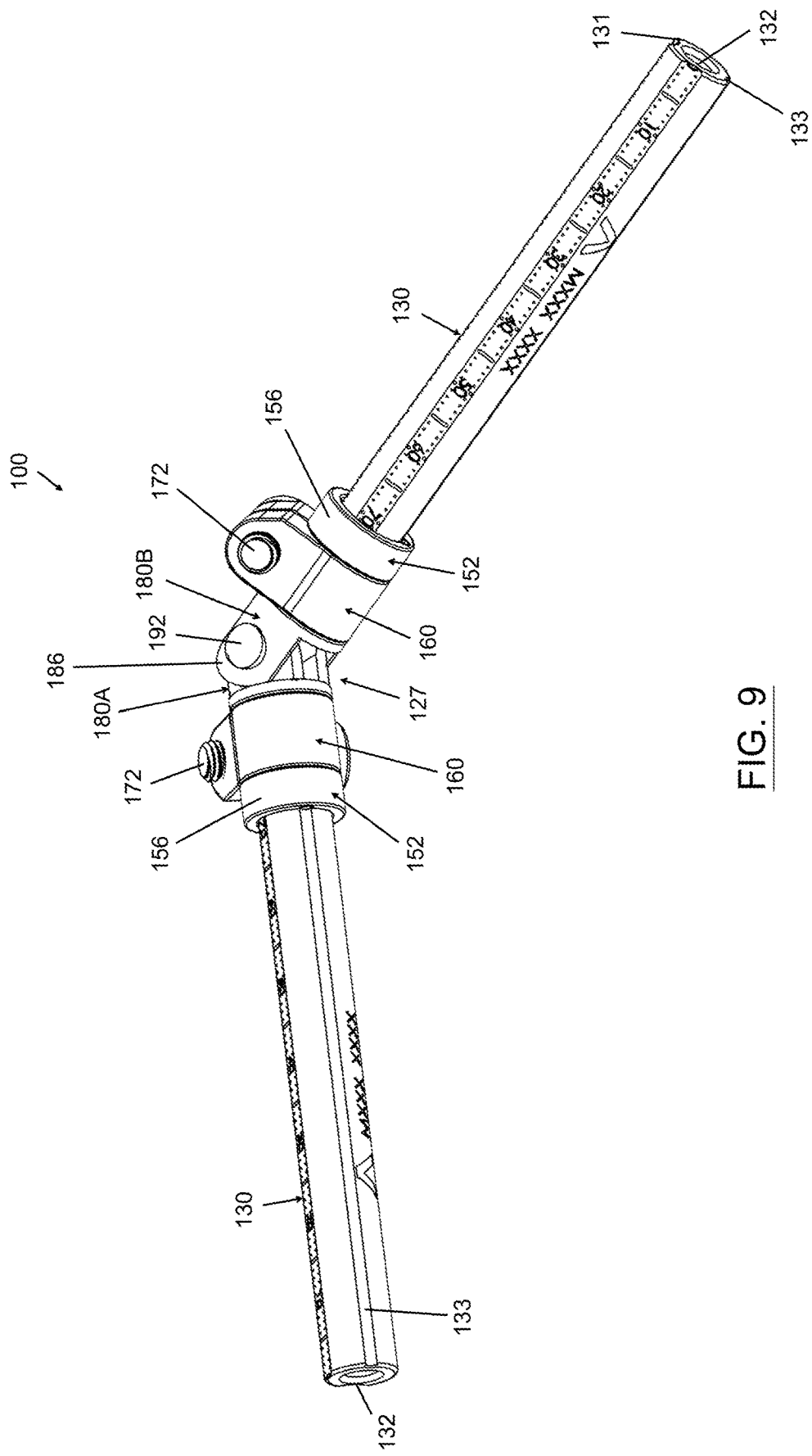
FIG. 9 illustrates a bottom perspective view of the exemplary adjustable rail apparatus of FIG. 6 in a non-linear arrangement, in accordance with the present disclosure.
Figure 12:
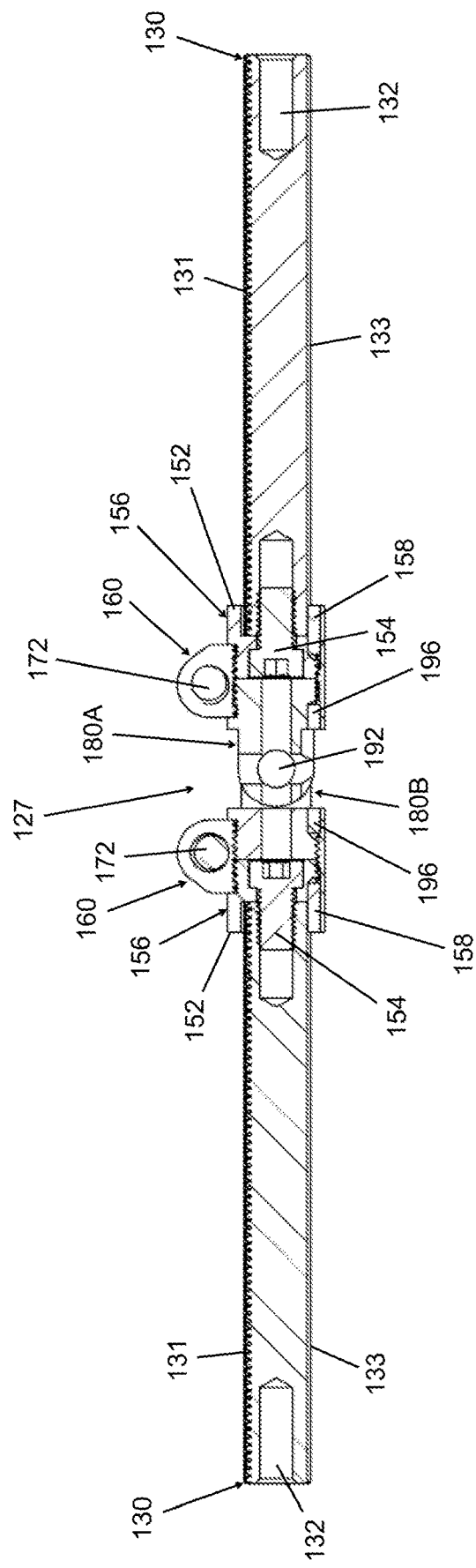
FIG. 12 illustrates a side cross-sectional view of the exemplary adjustable rail apparatus of FIG. 6 in a linear arrangement along Line 12-12 of FIG. 11, in accordance with the present disclosure.
Figure 13:
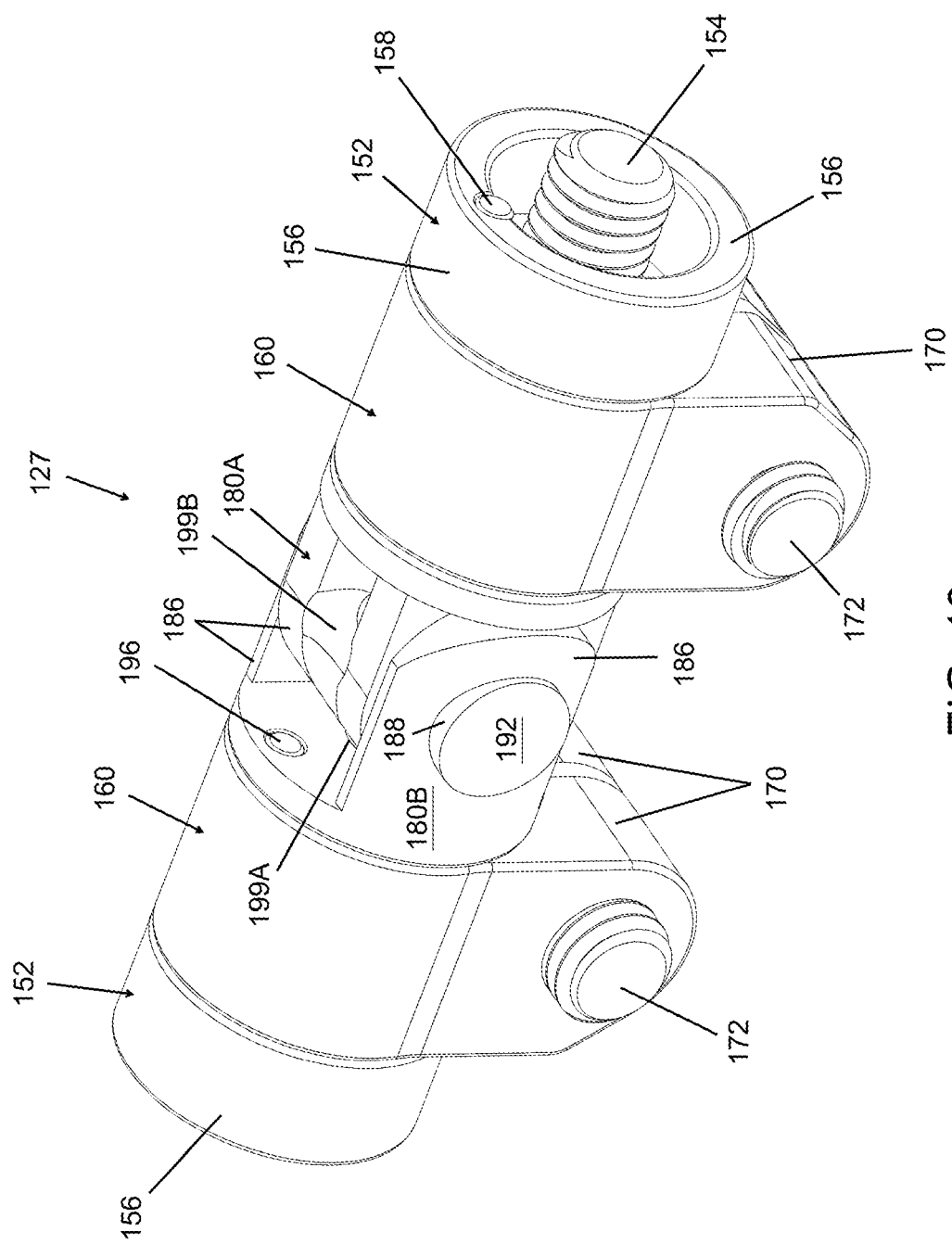
FIG. 13 illustrates an elevational perspective view of the exemplary adjustable hinge of the adjustable rail apparatus of FIG. 6 in a linear arrangement, in accordance with the present disclosure.
Figure 14:
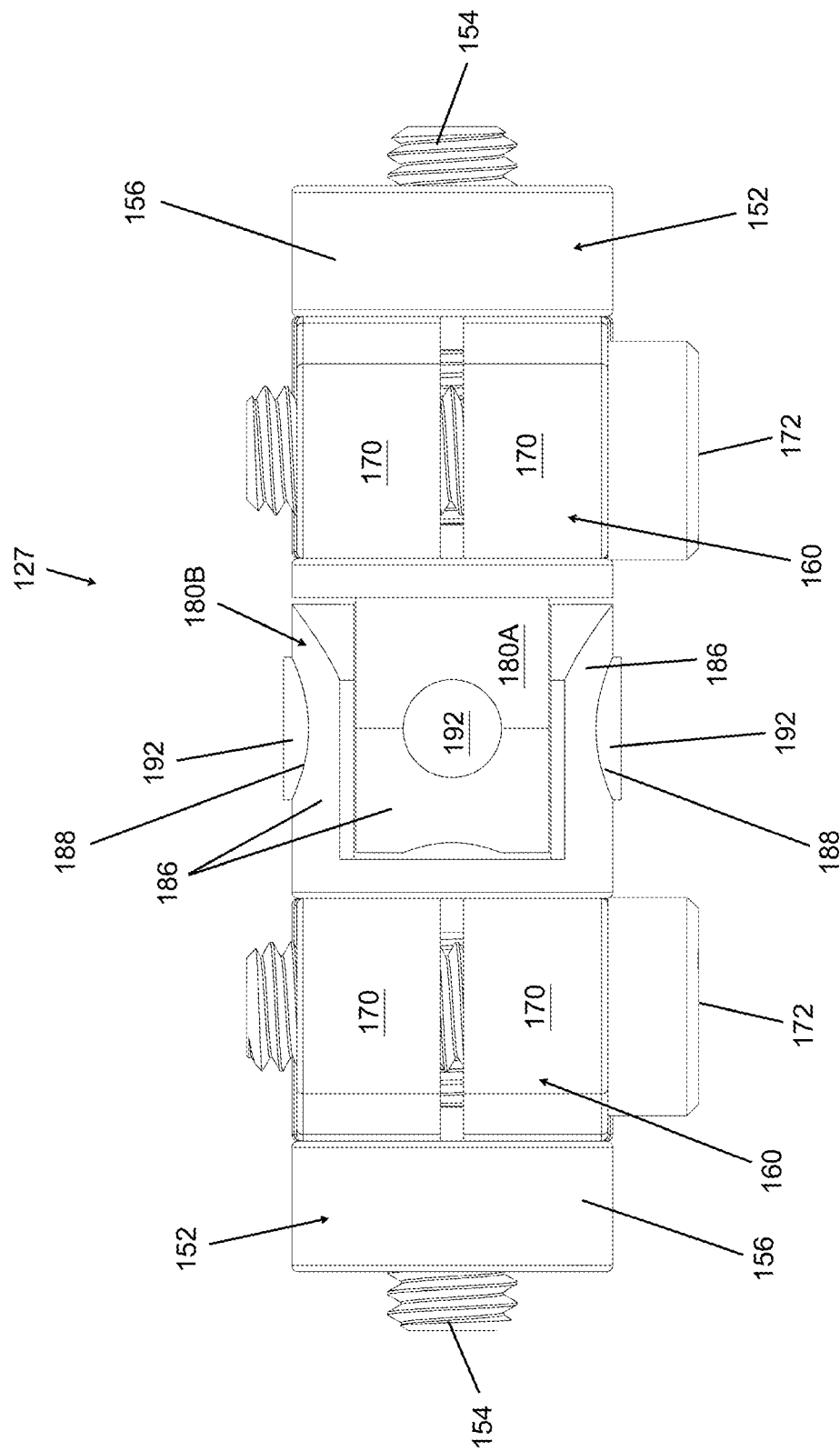
FIG. 14 illustrates a top view of the exemplary adjustable hinge of FIG. 13 in a linear arrangement, in accordance with the present disclosure.
Figure 15:
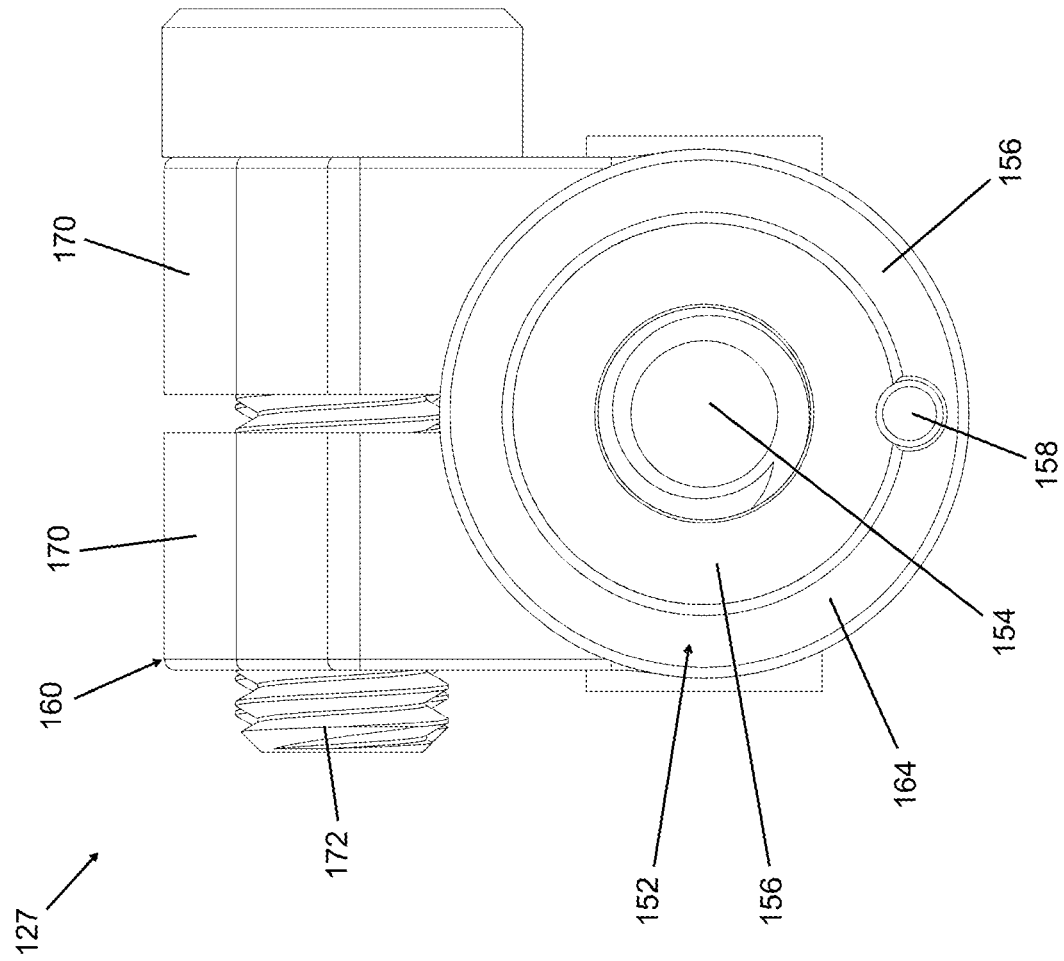
FIG. 15 illustrates an end view of the exemplary adjustable hinge of FIG. 13 in a linear arrangement, in accordance with the present disclosure.
Figure 16:
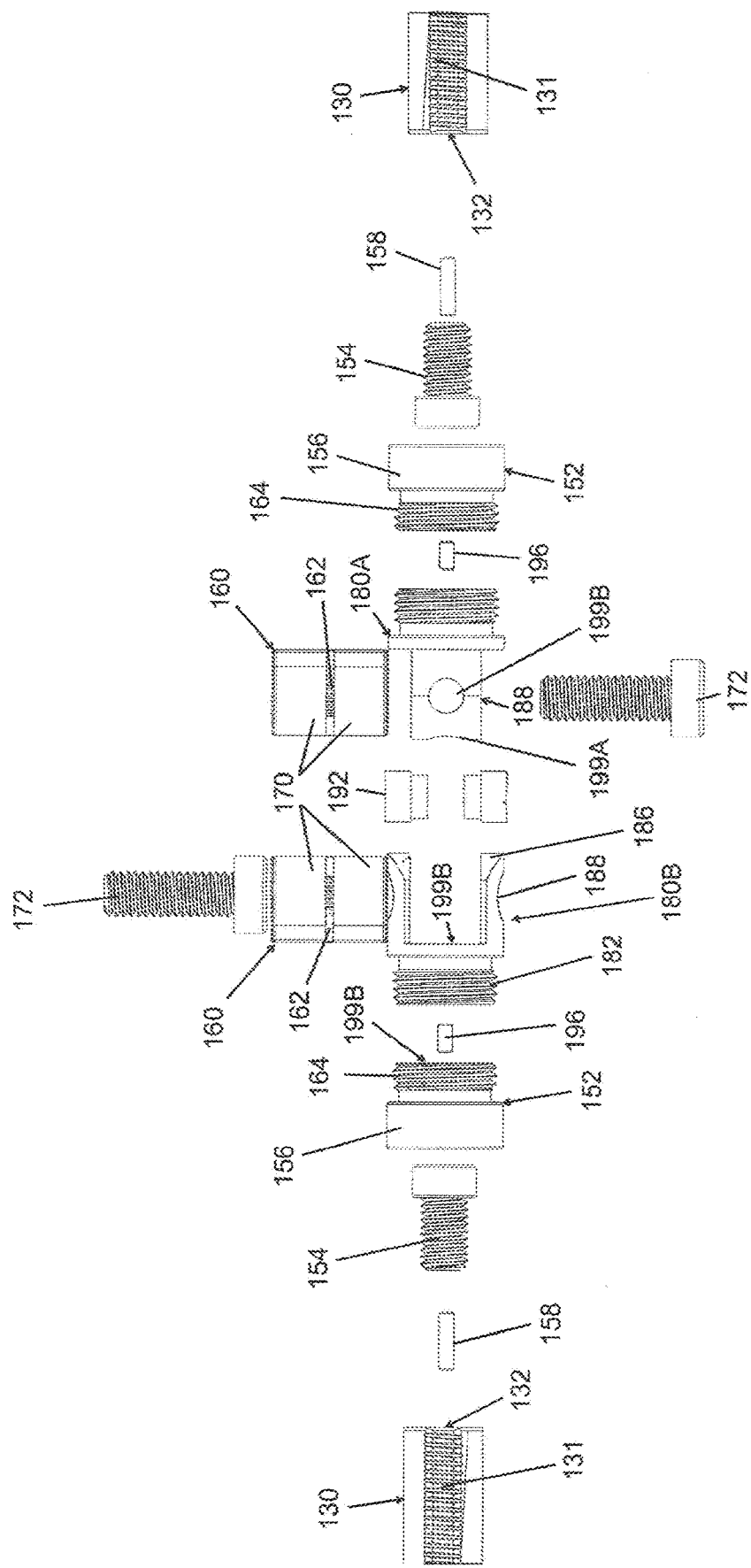
FIG. 16 illustrates an exploded side view of a portion of the exemplary adjustable rail apparatus of FIG. 6 including the exemplary adjustable hinge thereof, in accordance with the present disclosure.
Figure 17:
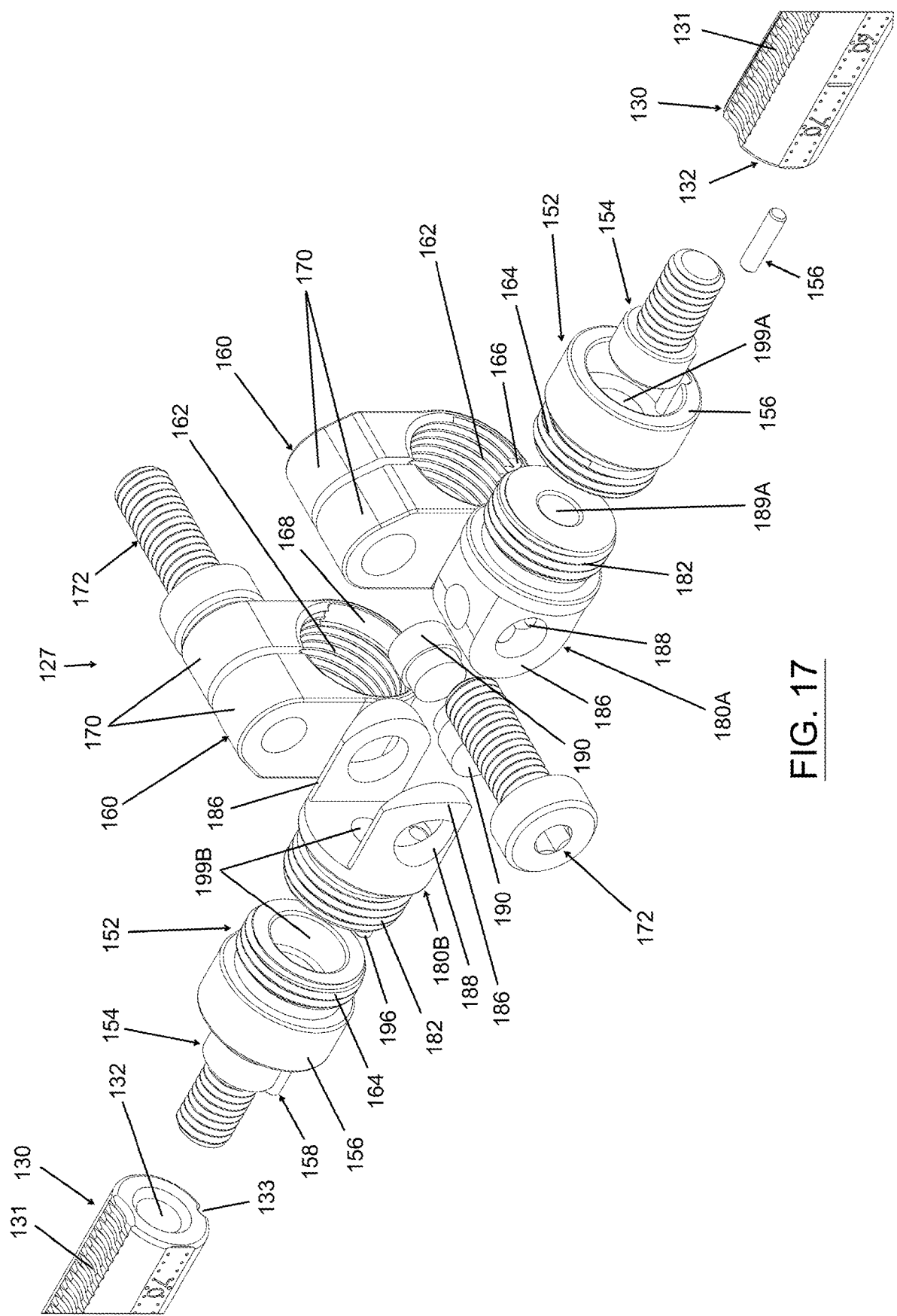
FIG. 17 illustrates an exploded elevational perspective view of a portion of the exemplary adjustable rail apparatus of FIG. 6 including the exemplary adjustable hinge thereof, in accordance with the present disclosure.
Figure 18:
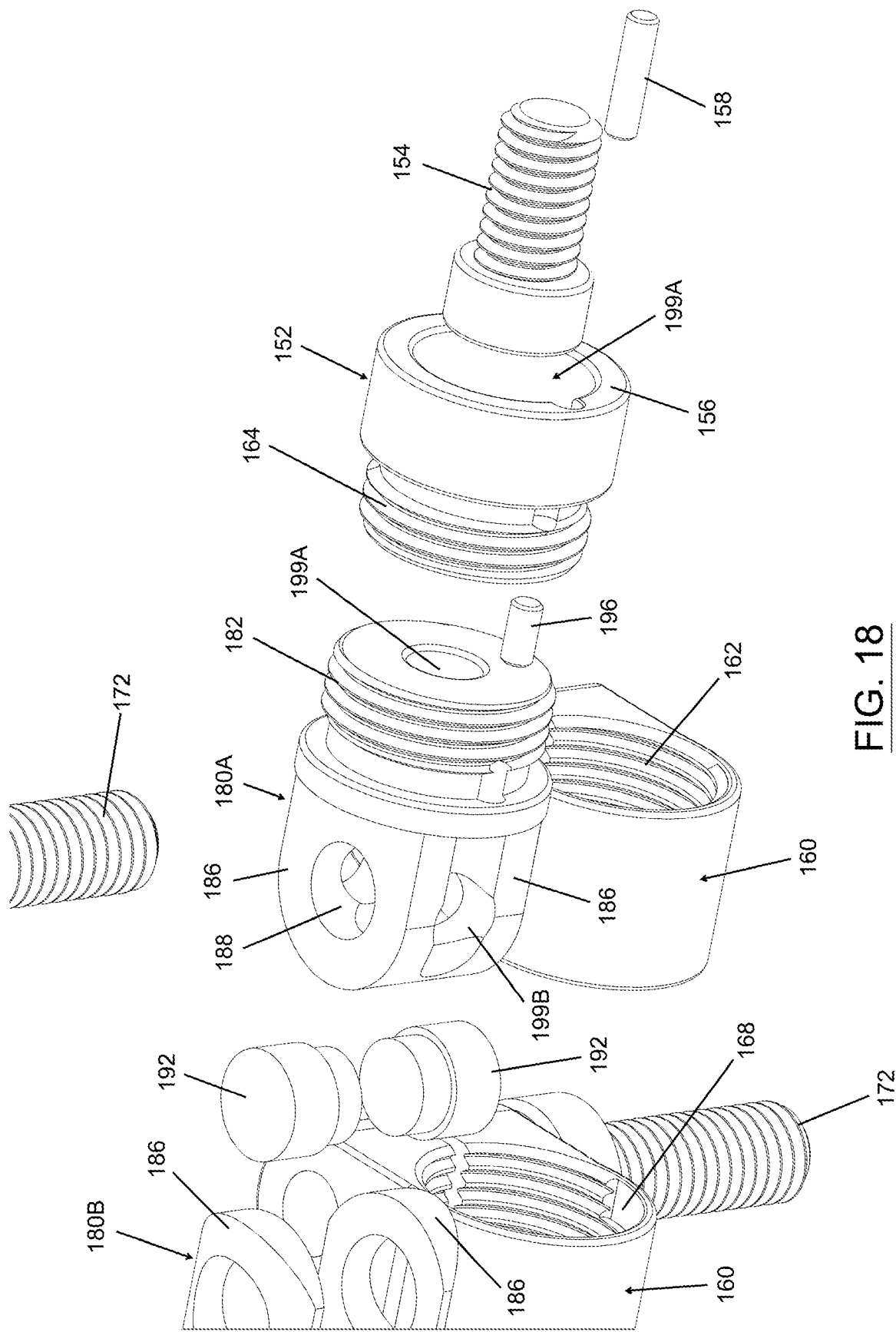
FIG. 18 illustrates an exploded elevational perspective view of a portion of the exemplary adjustable hinge of the exemplary adjustable rail apparatus of FIG. 6, in accordance with the present disclosure.
Figure 19:
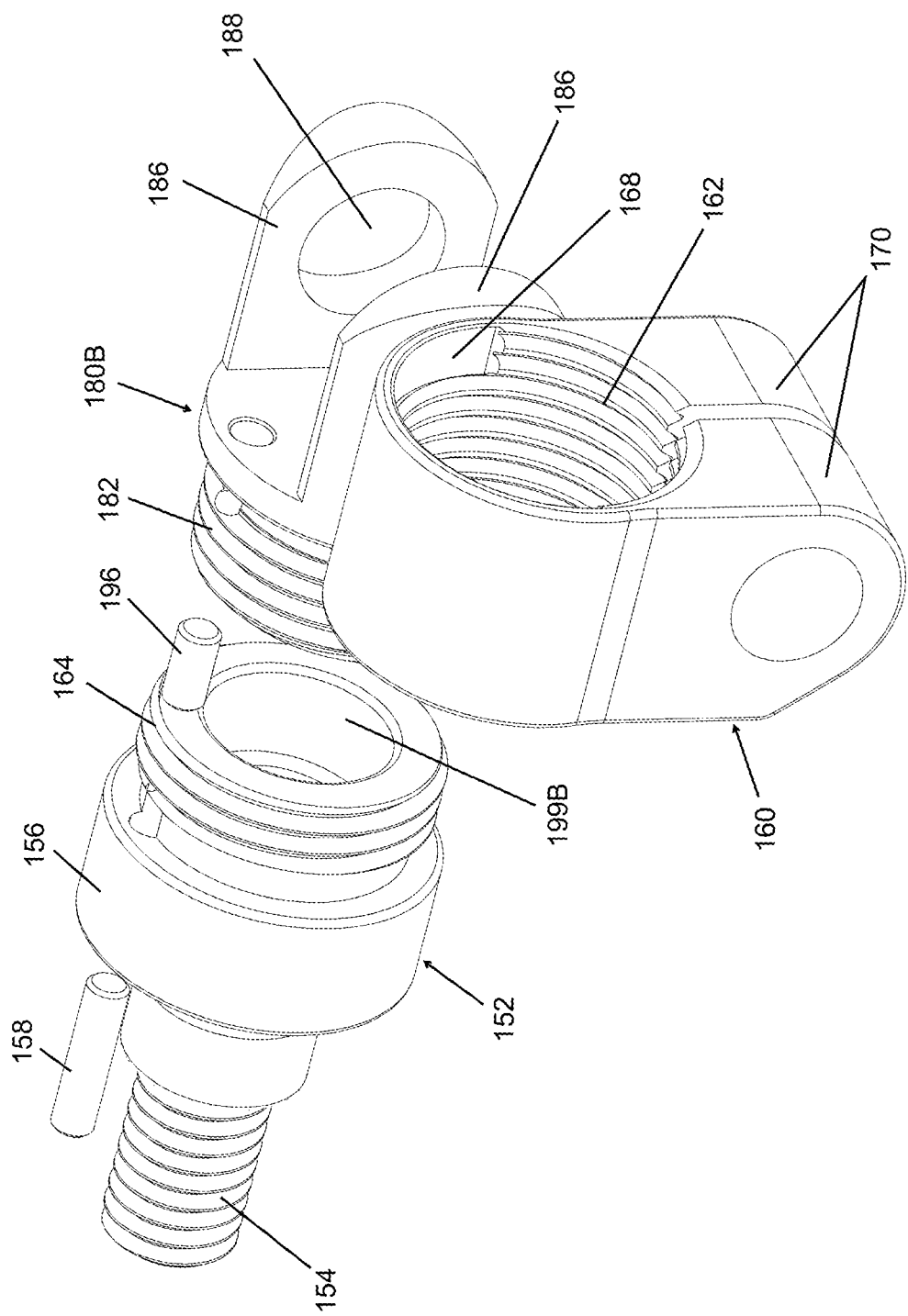
FIG. 19 illustrates an exploded elevational perspective view of another portion of the exemplary adjustable hinge of the exemplary adjustable rail apparatus of FIG. 6, in accordance with the present disclosure.
Figure 20:
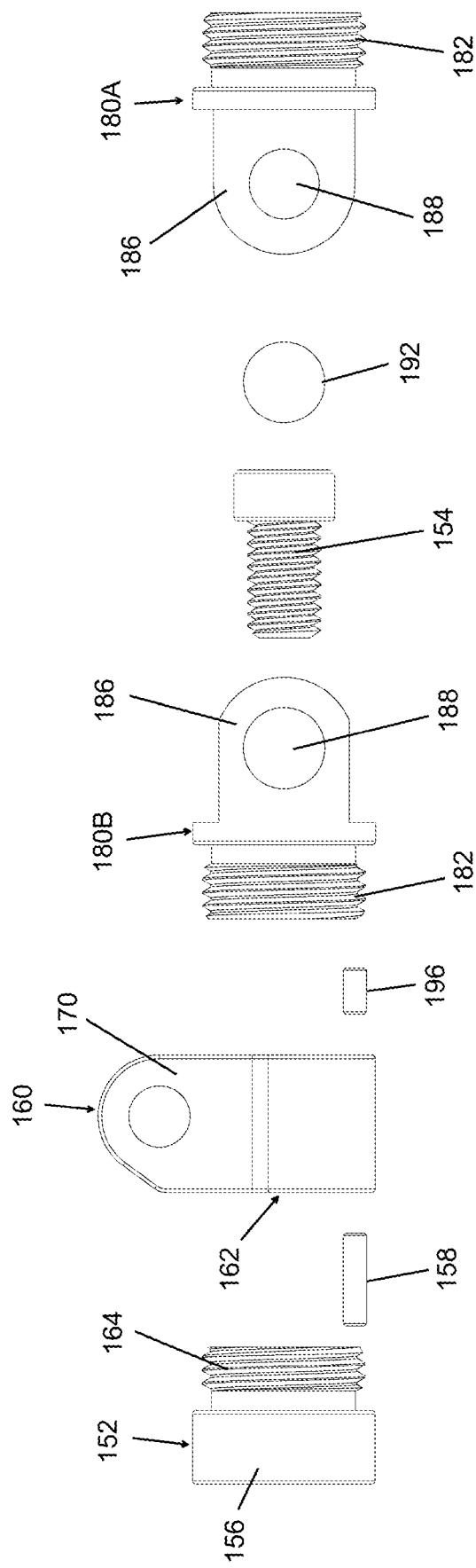
FIG. 20 illustrates an exploded side view of a portion of the exemplary adjustable hinge of the exemplary adjustable rail apparatus of FIG. 6, in accordance with the present disclosure.
Figure 21:
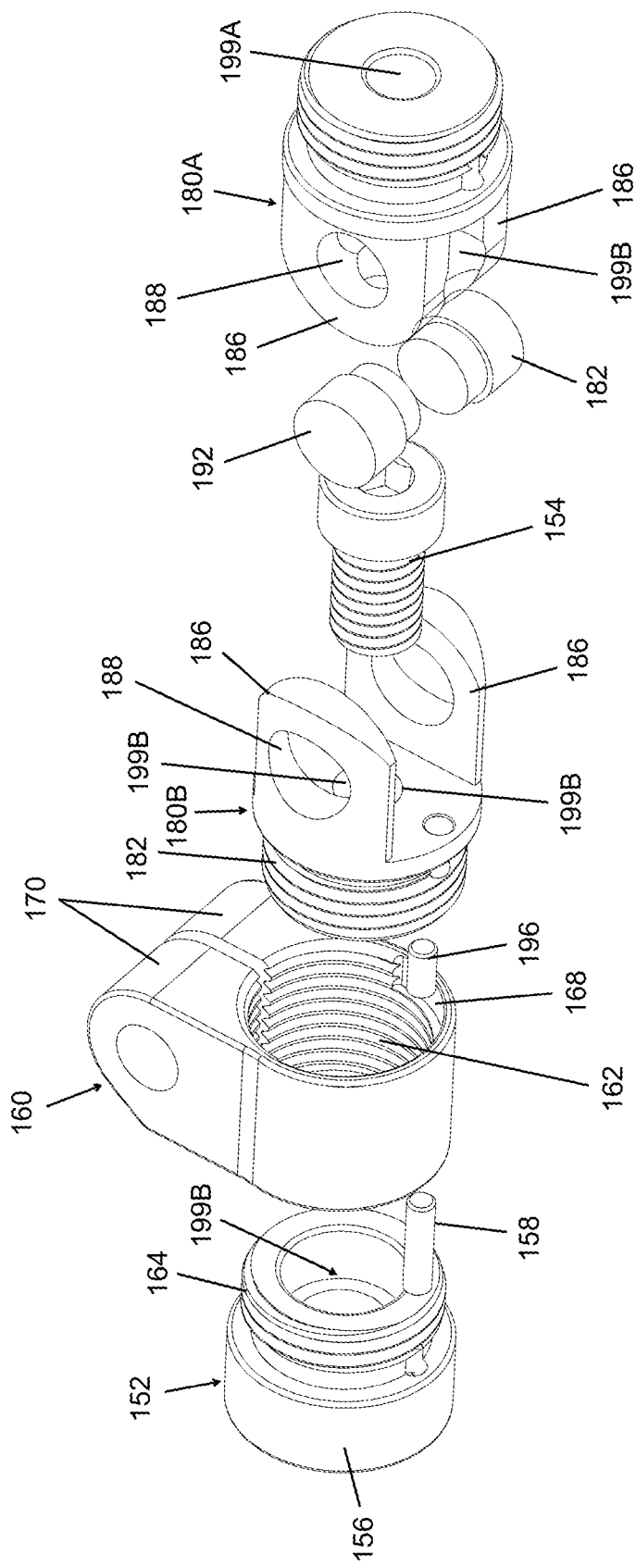
FIG. 21 illustrates an exploded perspective view of the portion of the exemplary adjustable hinge of the exemplary adjustable rail apparatus of FIG. 20, in accordance with the present disclosure.
Figure 22:
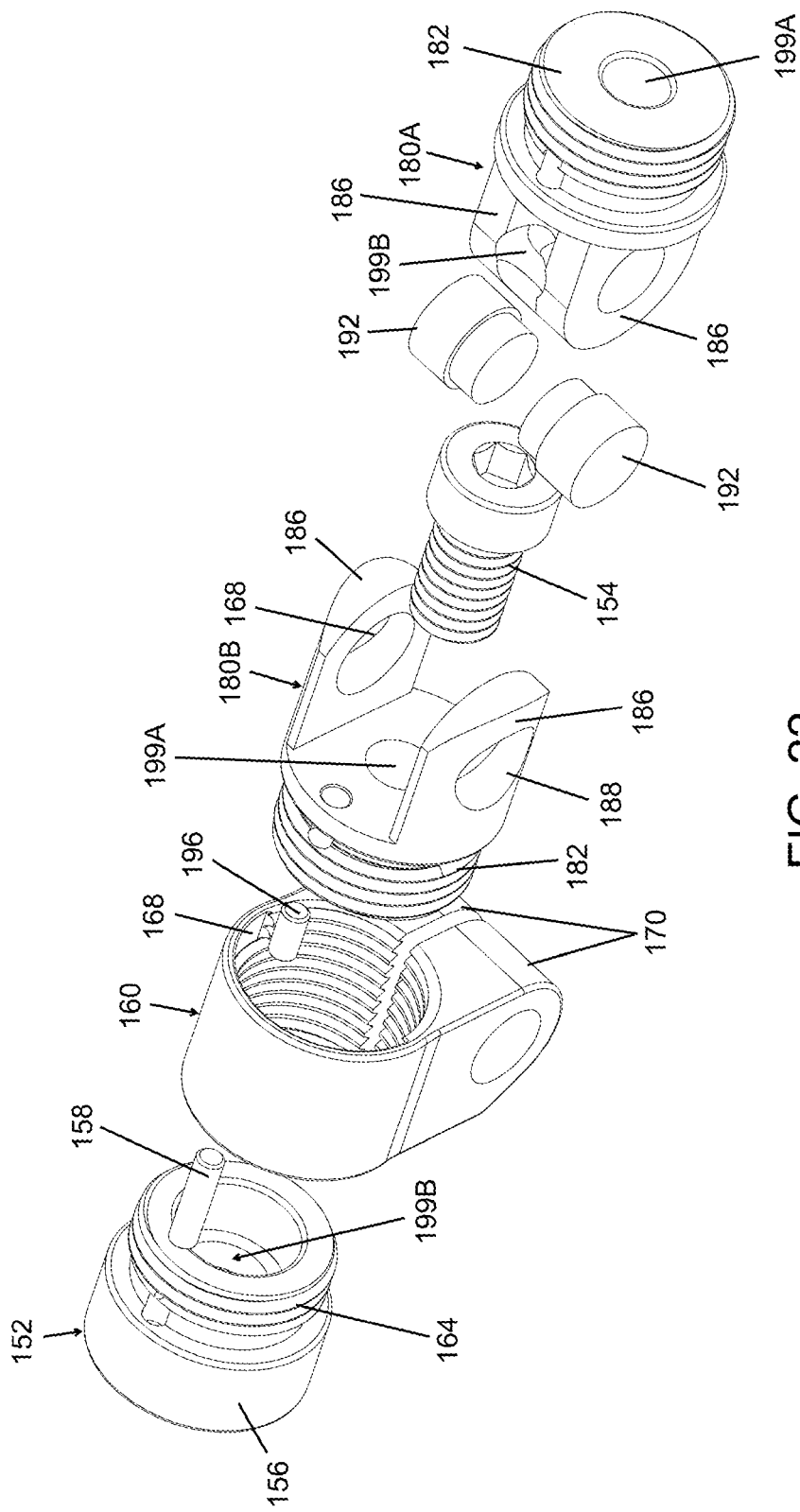
FIG. 22 illustrates an exploded elevational perspective view of the portion of the exemplary adjustable hinge of the exemplary adjustable rail apparatus of FIG. 20, in accordance with the present disclosure.

As shown in the linear and aligned first configuration of the beam elements 130 of the adjustable beam apparatus 125 as shown in FIGS. 6 and 7 as compared to the non-linear/angled and rotated second configuration of the beam elements 130 of the adjustable beam apparatus 125 of FIGS. 3 and 4 as shown in FIGS. 8 and 9, the hinge mechanism 127 allows a user to adjust or configure the angle of the axes of the beam elements 130 with respect to each other and/or the relative orientations of the beam elements 130 about their axes (with respect to each other).

As shown in FIGS. 6-26, the hinge mechanism 127 may include beam end housings 152 that axially fix or couple to an end portion 132 of the beam element 130. For example, the beam end housings 152 may include a through aperture that is configured to allow a threaded post portion of a cap screw 154 to extend therethrough and threadably couple with a threaded internal aperture 132 extending into the end of a respective beam element 130, as shown in FIGS. 4, 5, 12-22, 25 and 26. The through aperture of the beam end housings 152 may also be configured to prevent a head portion of the cap screws 154 to travel/translate (axially) therethrough. The head portion of the cap screws 154 may also include a rotation depression, aperture, projection or other feature that allows the cap screws 154 to be engaged and be rotated or torqued (about an axis thereof) to screw the threaded post portions extending through/past the aperture of the beam end housings 152 into the internal aperture 132 of a respective beam element 130.

As shown in FIGS. 6-26, the hinge mechanism 127 may be configured or provided such that the cap screws 154 are trapped or housed within the beam end housings 152, and the rotation feature thereof is accessible (e.g., along the rotation axis of the cap screws 154 via one or more through apertures) via access apertures 199A, 199B in at least one relative configuration or arrangement of the hinge mechanism 127, as shown in FIGS. 23-26, so that the hinge mechanism 127 can be coupled between/to the ends portions 132 of a pair of the beam elements 130, as described further below. In this way, the hinge mechanism 127 may initially be provided separately/individually or de-coupled from the pair of the beam elements 130, and subsequently coupled thereto via threading the cap screws 154 (via rotation) into the internal apertures 132 of the beam element 130.

As shown in FIGS. 6-26, the beam end housings 152 may include a sleeve portion 156 that extends at least partially about the exterior surface of the end portion 132 of a beam element 130 (e.g., when the adjustment hinge 127 is coupled thereto via the cap screws 154). As shown in FIGS. 12, 13 and 16-22, the sleeve portion 156 of the beam end housings 152 may include a projection or pin 158 that engages within the groove 133 of a beam element 130 (e.g., when the adjustment hinge 127 is coupled thereto via the cap screws 154) to rotationally lock the beam end housings 152 and the beam elements 130 together (i.e., prevent the beam end housings 152 from rotating about the axis of the respective beam elements 130). As shown in FIGS. 12, 13 and 16-22, in one exemplary embodiment the projection 158 may comprise a pin or like member that is positioned or captured within, and extends from, an aperture or slot within an interior surface of the sleeve portion 156 of the beam end housings 152.

The sleeve portion 156 of the beam end housings 152 and the projections 158 may be configured to be axially translated onto an end portion 132 of the beam elements 130 via rotation of the cap screws 154 (i.e., threadably coupled with the internally threaded axial aperture of the end portion 132 of the beam elements 130) such that the end portion 132 of the beam element 130 is received/positioned within the sleeve portion 156 and the projection 158 is seated within the recess 133 of the beam element 130. The beam end housings 152 may thereby be axially and rotationally fixed with respect to a respective beam element 130.

As shown in FIGS. 6-26, the adjustment hinge 127 may also include a pair of split clamp collars 160. Each split clamp collar 160 includes an internally threaded axial internal bore 162 configured to threadably mate with an externally threaded post portion 164 of a respective beam end housing 152 and an externally threaded post portion 182 of a respective rotation end housing 180A, 180B to axially fix each clamp collar 160 with a respective beam end housing 152, a respective rotation end housing 180A, 180B and a respective beam element 130 (via a respective cap screw 154), as shown in FIGS. 12 and 16-22. The threaded post portion 164 of the beam end housing 152 is provided/positioned at one axial end of the beam end housing 152, and the sleeve portion 156 thereof is provided/positioned the other axial end of the beam end housing 152, as shown in FIGS. 12 and 16-22.

A distal axial side of the threaded internal bore 162 of each clamp collar 160 may include a recess or non-threaded portion 166 that mates with the projection or pin 158 mounted on/associated with the respective beam end housing 152 (when the externally threaded post portion 164 of the respective beam end housing 152 is threadably coupled with the distal axial side of the threaded internal bore 162), as shown in FIGS. 12, 17-19, 21 and 22. For example, each beam end housing 152 may be configured with an aperture and/or slot that houses the projection or pin 158 that extends, partially, on the inner/interior side of the sleeve portion 156 and the outer/exterior side of the post portion 164, as shown in FIGS. 12, 17-19, 21 and 22. The recess or non-threaded portion 166 of the threaded internal bore 162 of the clamp collar 160 and the portion of the projection or pin 158 mounted on/associated with the outer side of the threaded post portion 164 of the beam end housing 152 are configured such that when the projection 158 is seated within the recess 166, the clamp collar 160 and the beam end housing 152 are rotationally fixed (about the axis of the beam elements 130), as shown in FIGS. 12, 17-19, 21 and 22. For example, the width of the recess or non-threaded portion 166 of the threaded internal bore 162 of the clamp collar 160 may match or substantially correspond to that of the projection or pin 158 mounted on/associated with the outer side of the threaded post portion 164 of the beam end housing 152.

Similarly, a proximal axial side of the threaded internal bore 162 of each clamp collar 160 may include a recess or non-threaded portion 168 that mates with a projection or pin 196 mounted on/associated with a threaded post portion 182 of a respective rotation end housing 180A, 180B (when the externally threaded post portion 182 of the respective rotation end housing 180A, 180B is threadably coupled with the proximal axial side of the threaded internal bore 162), as shown in FIGS. 12, 16-19, 21 and 22. For example, the threaded post portion 182 of each rotation end housing 180A, 180B may be configured with an aperture and/or slot that houses the projection or pin 196 that partially extends on the outer/exterior side of the post portion 182, as shown in FIGS. 12, 16-19, 21 and 22. The recess or non-threaded portion 168 of the threaded internal bore 162 of the clamp collar 160 and the portion of the projection or pin 196 mounted on/associated with the outer side of the threaded post portion 182 of the rotation end housing 180A, 180B are configured such that when the projection or pin 196 is seated within the recess or non-threaded portion 168, only a limited about of relative rotation of the respective rotation end housing 180A, 180B within the internal bore 162 of the clamp collar 160 (and thereby about the axis of the beam elements 130) is provided, as shown in FIGS. 12, 16-19, 21 and 22. For example, the width of the recess or non-threaded portion 168 of the threaded internal bore 162 of the clamp collar 160 may be substantially larger or longer than that of the projection or pin 196 mounted on/associated with the outer side of the threaded post portion 182 of the respective rotation end housing 180A, 180B, as shown in FIGS. 17, 18, 21 and 22. In this way, the relative rotational arrangement or orientation of an associated beam element 130 with respect to a respective rotation end housing 180A, 180B (and thereby the pivot or rotation point or axis, as explained further below) can be adjusted or chosen within the range provided for/by the recess 168 via relative rotation of the respective clamp member 160, beam end housing 156 and beam element 130 (e.g., about the axes thereof).

When a particular relative rotational arrangement or orientation of a beam element 130 and a respective rotation end housing 180A, 180B, such as with respect to the joint 127 generally (e.g., the pivot or rotation point or axis of the joint 127, as explained further below) and/or the respective clamp collar 160 is selected or achieved, the respective split clamp collar 160 can utilized to selectively lock the particular rotational arrangement. As shown in FIGS. 6-26, the split clamp collars 160 include clamping portions 170 that are separated by a gap or split that passes from the exterior of the clamp collars 160 to the central bore 162 along the entirety of the axial length thereof. The clamping portions 170 may include substantially aligned through apertures with axes that extend across the gap between the clamping portions 170, as shown in FIGS. 6-26. At least one of the through apertures of the clamping portions 170 may be threaded, and the through apertures may be configured to mate with a clamping or compression screw 172, as shown in FIGS. 6-26. The clamp collars 160 and the clamping screws 172 may be configured such that when a clamping screw 172 is rotated or axially advanced into/through the aperture of the clamping portions 170 and across the gap of a clamp collar 160, the clamping portions 170 are drawn together and the central bore 162 is compressed (i.e., the diameter or width of the central bore 162 thereof is made smaller) such that the clamp collar 160 applies a compressive force to the associated threaded post portion 164 of a respective rotation end housing 180A, 180B to rotationally fix (e.g., about the axis of the associated beam element 130) the associated threaded post portion 164 of the respective rotation end housing 180A, 180B and the respective clamp collar 160.

In this way, the relative rotational arrangement or orientation of a respective beam element 130 with respect to a respective rotation end housing 180A, 180B (and thereby the pivot or rotation point or axis of the joint 127, as explained further below) can be selectively fixed via the clamping or compression force applied to the threaded post portion 164 of the respective rotation end housing 180A, 180B via the clamp collar 160 as the clamp collar 160 is rotationally fixed to a respective beam end housing 156 and a beam element 130 associated therewith, as described above. Conversely, the relative rotational arrangement or orientation of a respective beam element 130 with respect to a respective rotation end housing 180A, 180B (and thereby the pivot or rotation point or axis of the joint 127, as explained further below) can be selectively provided or adjusted via reducing (or eliminating) the clamping or compression force applied to the threaded post portion 164 of the respective rotation end housing 180A, 180B via the clamp collar 160 (via rotation of the clamping screw 172), and rotating the respective beam element 130 (and the associated clamp collar 160 and beam end housing 152 rotationally fixed thereto) about its axis with respect to the respective rotation end housing 180A, 180B (and thereby the pivot or rotation point or axis of the joint 127, as explained further below).

In some embodiments, the split clamp collars 160 may be deformed via rotation of the clamping screw 172 such that the clamping portions 170 are moved closer toward each other (i.e., the gap is decreased) and, thereby, the diameter or other size of the central bore 162 is decreased to apply the compressive force to the threaded post portion 164 of a respective beam end housing 152 and a threaded post portion 164 of a respective rotation end housing 180A, 180B (to rotationally fix the components).

As shown in FIGS. 12-14 and 16-22, the rotation end housings 180A, 180B each include a joint or rotation portion 186 that are rotationally or pivotably coupled or mated via at least one joint pin 192 extending through aligned apertures 188 thereof. As shown in FIGS. 12-14 and 16-22, the rotation portions 186 of the rotation end housings 180A, 180B and the at least one joint pin 192 may form a U-joint such that the second rotation end housing 180B comprises a "U" or split flange yoke and the first rotation end housing 180A forms a shaft portion that fits and rotates within the rotation end housing 180B (or vice versa). The at least one joint pin 192 (e.g., at least one stepped pin) may extend through the apertures 188 of the rotation portion 186 of the second rotation end housing 180B and at least partially through the aperture(s) 188 of the rotation portion 186 of the first rotation end housing 180A. The at least one pin 192 may rotationally fix the rotation portions 186 of the first and second rotation end housings 180A, 180B together, but allow for pivoting or angular rotation therebetween along an axis that is angled with respect to the axes of the beam elements 130. For example, the at least one joint pin 192 may fix the rotation portions 186 of the first and second rotation end housings 180A, 180B together (and thereby the associated beam elements 130 together) along the axes of the associated beam elements 130, but allow angular/pivoting movement therebetween (and thereby between the associated beam elements 130) about the axis of the at least one joint pin 192, as shown by the arrangement of the joint 127 in FIGS. 6 and 7 as compared to FIGS. 8 and 9.

The axis of the angular movement or rotation between the rotation portions 186 of the first and second rotation end housings 180A, 180B, and thereby the associated beam elements 130, provided by the at least one joint pin 192 (i.e., the axis of the at least one joint pin 192) is thereby angled with respect to the axis of the associated beam elements 130. In some embodiments, the axis of the angular movement or rotation between the first and second rotation end housings 180A, 180B (i.e., the axis of the at least one joint pin 192) (and thereby between the associated beam elements 130) intersects the axes of the associated beam elements 130. In some embodiments, the axis of the angular movement or rotation between the first and second rotation end housings 180A, 180B (i.e., the axis of the at least one joint pin 192) (and thereby between the associated beam elements 130) is oriented normal or perpendicular to the axes of the associated beam elements 130.

As also shown in FIGS. 6-26, the first rotation end housing 180A may include first and second coupling apertures 199A, 199B extending therethrough from the rotation portion 186. The first coupling aperture 199A of the first rotation end housing 180A may be at least partially aligned with the axis of the coupling cap screw 154 captured within the associated beam end housing 152. Similarly, the associated beam end housing 152 may also include a first coupling aperture 199A that is at least partially aligned with the first coupling aperture 199A of the first rotation end housing 180A and the axis of the coupling cap screw 154 captured therein. In this way, when the hinge mechanism 127 is configured/arranged (e.g., the angular orientation of the beam elements 130 is configured/arranged) such that the first coupling aperture 199A at the rotation portion 186 of the first rotation end housing 180A is exposed or accessible, as shown in FIGS. 23-25, a tool may be inserted through the first coupling apertures 199A and into engagement with the coupling cap screw 154 to apply a torque thereto and, ultimately, threadably couple or de-couple the cap screw 154 (and thereby the first rotation end housing 180A and the hinge mechanism 127 as a whole) with the end aperture 132 of a first beam element 130.

Figure 23:
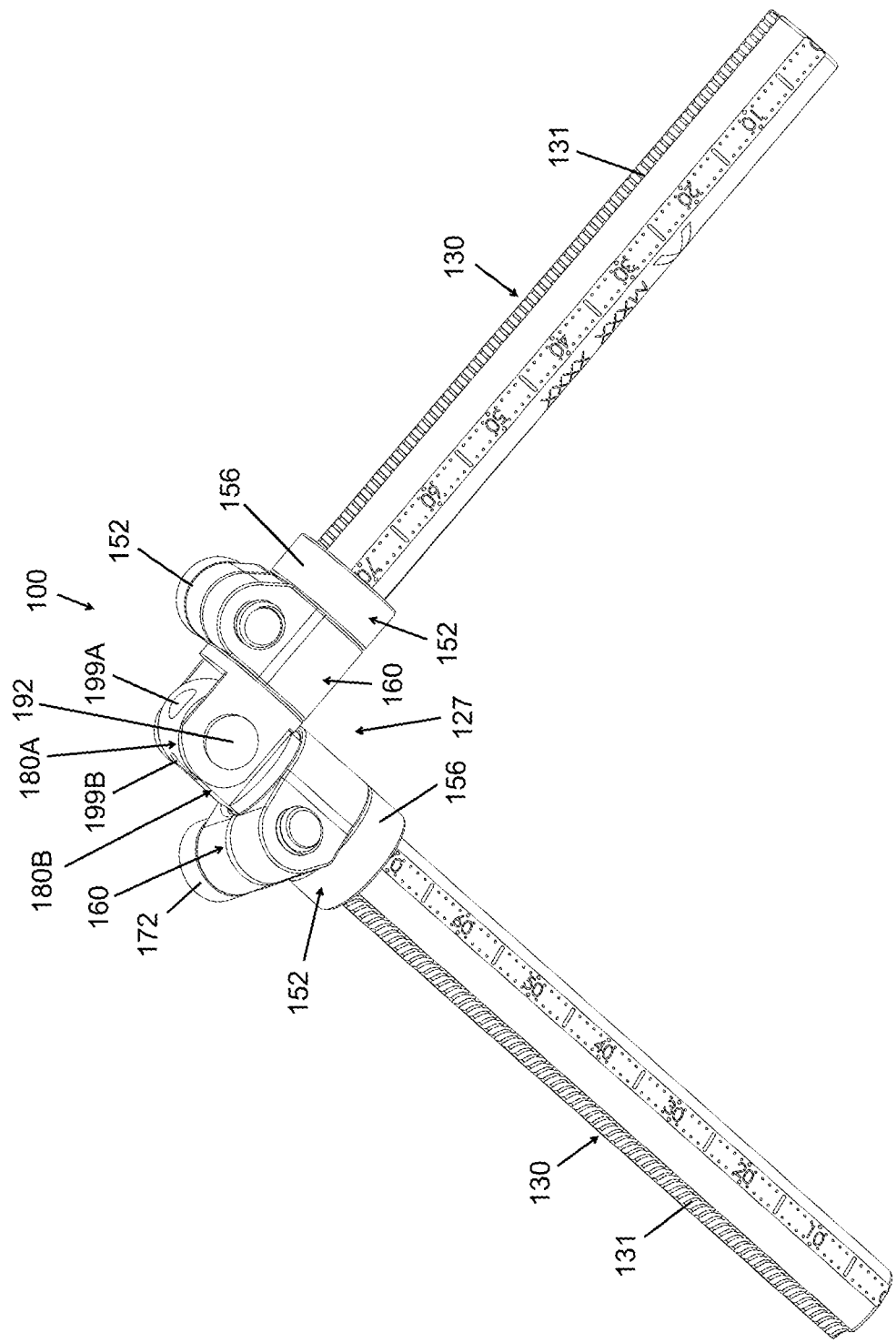
FIG. 23 illustrates a perspective view of the exemplary adjustable rail apparatus of FIG. 6 in a non-linear arrangement, in accordance with the present disclosure.
Figure 24:
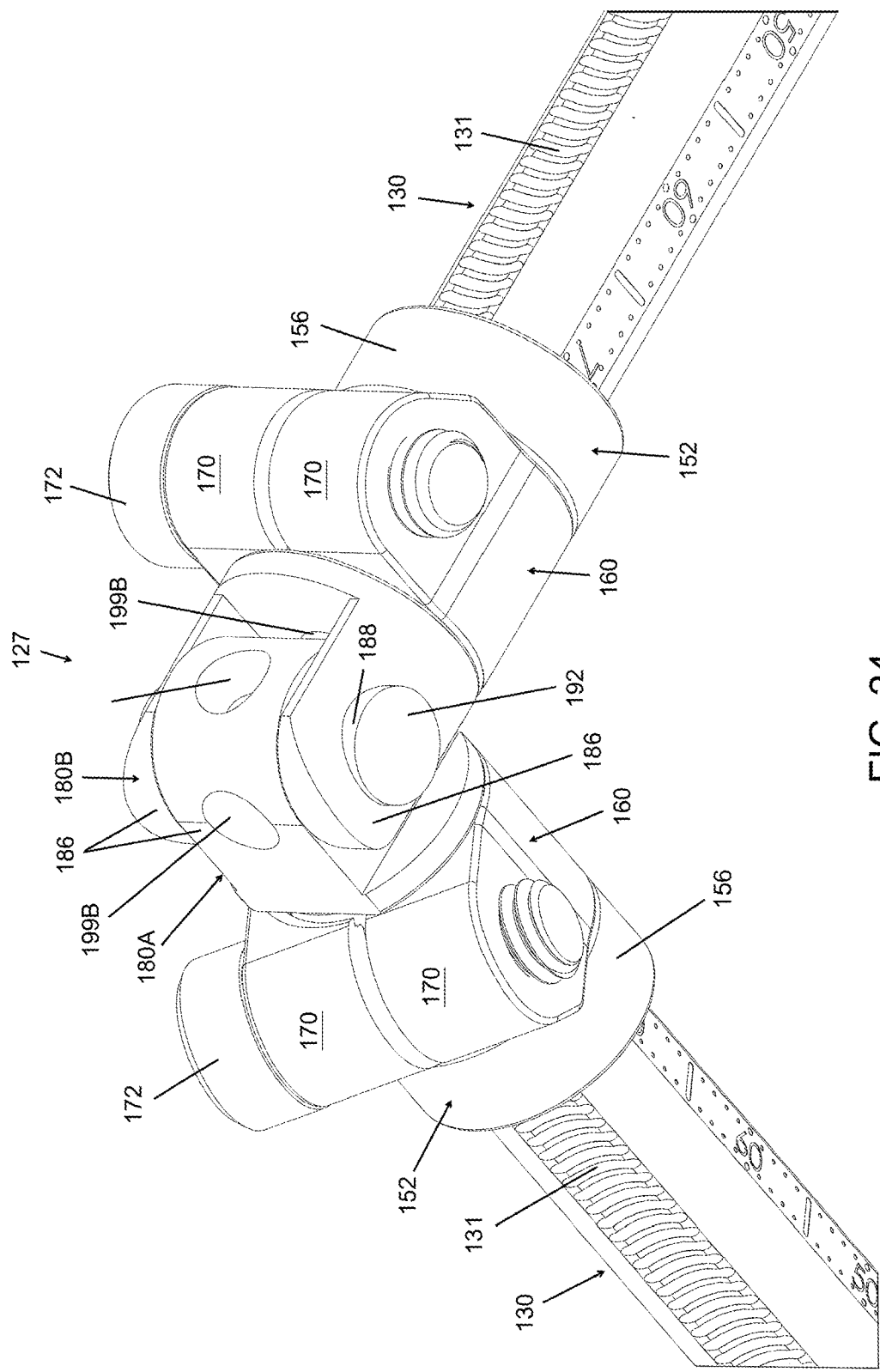
FIG. 24 illustrates an enlarged elevational perspective view of a portion of the exemplary adjustable rail apparatus of FIG. 6 including the exemplary hinge thereof in a non-linear arrangement, in accordance with the present disclosure.
Figure 25:
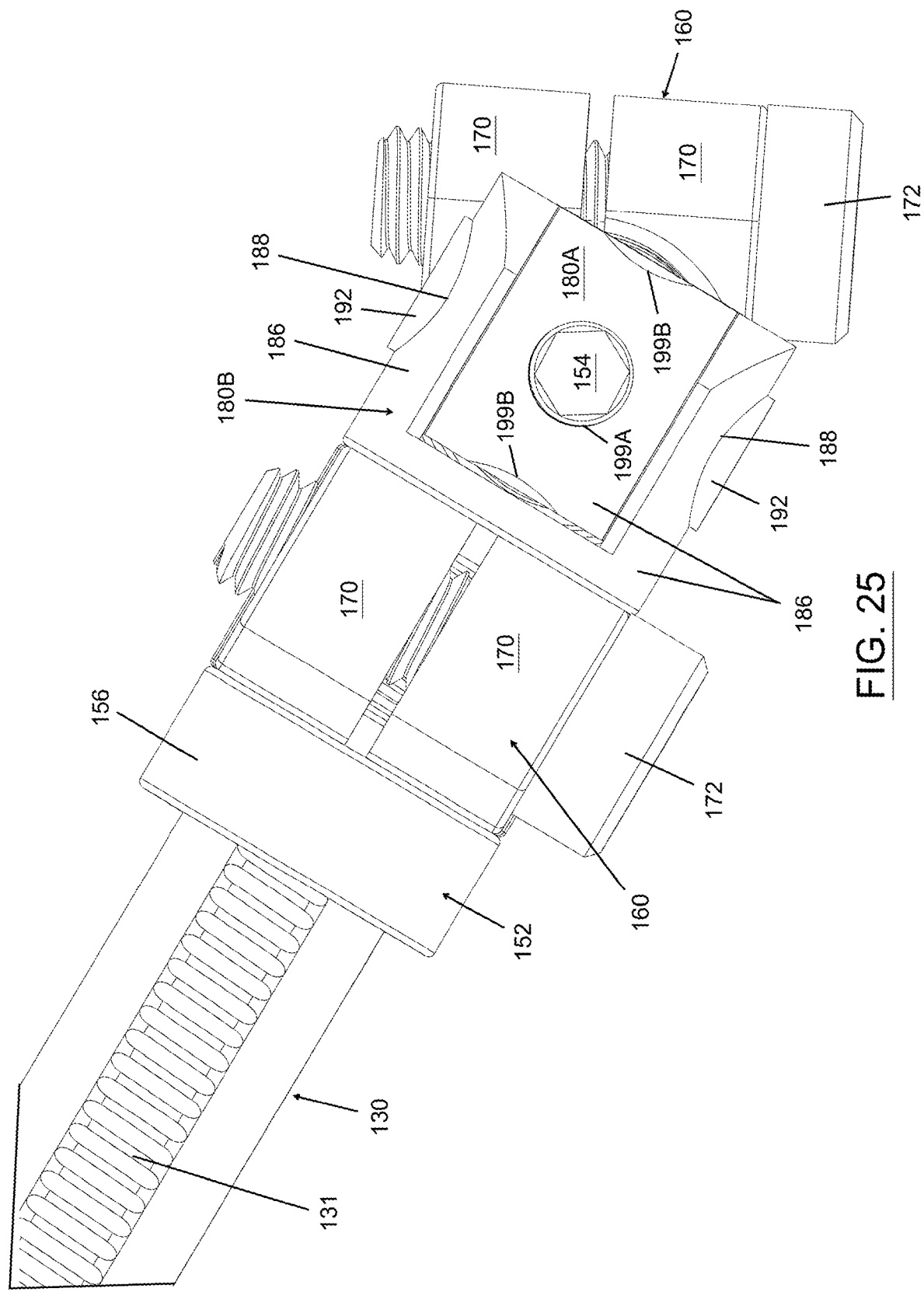
FIG. 25 illustrates an enlarged top view of a portion of the exemplary adjustable rail apparatus of FIG. 6 including the exemplary hinge thereof in a non-linear arrangement, in accordance with the present disclosure.
Figure 26:
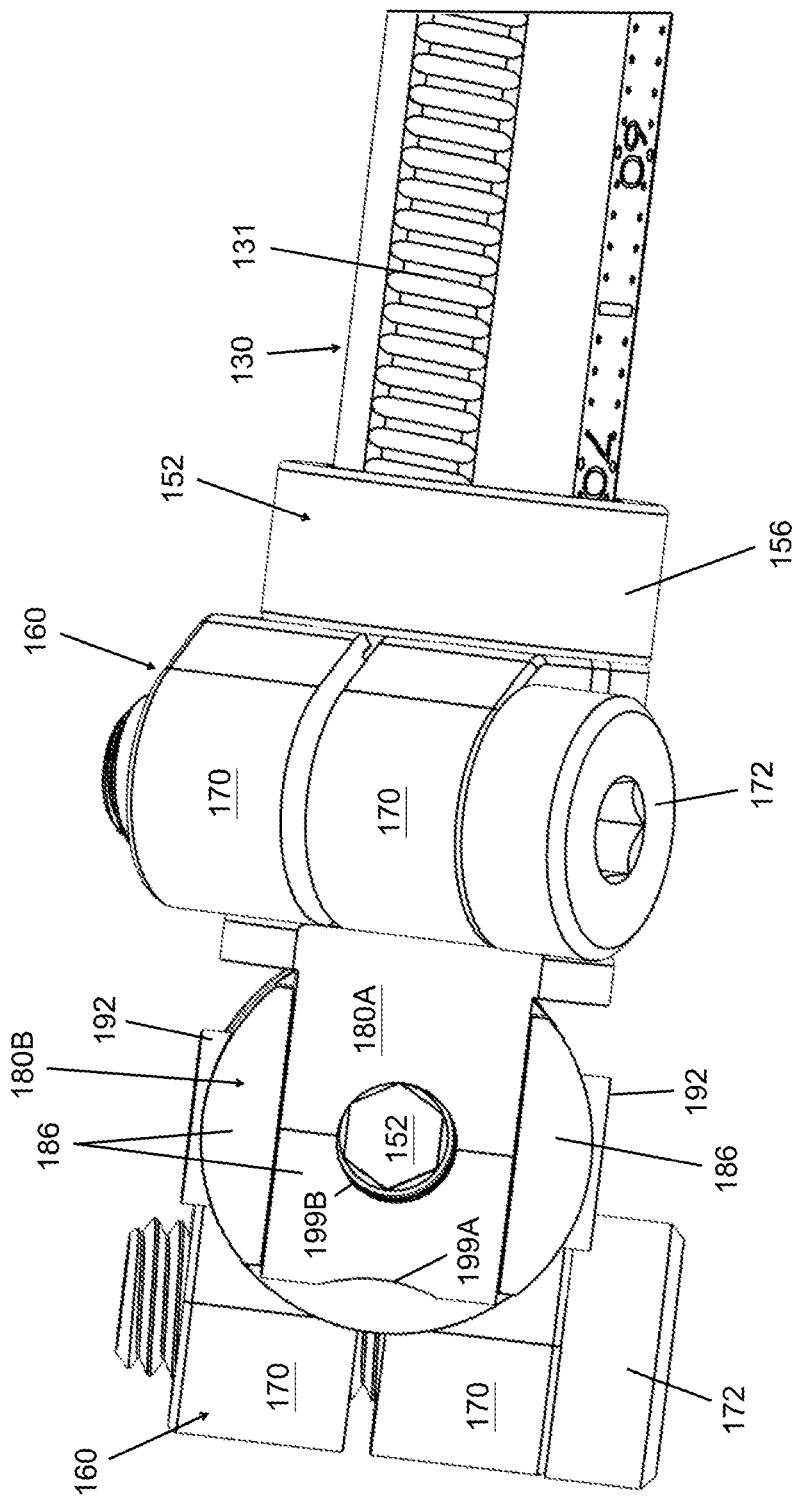
FIG. 26 illustrates an enlarged top view of another portion of the exemplary adjustable rail apparatus of FIG. 6 including the exemplary hinge thereof in a non-linear arrangement, in accordance with the present disclosure.

Similarly, the second coupling aperture 199B of the first rotation end housing 180A may be at least partially aligned with the axis of the coupling cap screw 154 captured within the beam end housing 152 associated with the second rotation end housing 180B in a particular arrangement or rotational arrangement of the first and second rotation end housings 180A, 180B about the axis of rotation (and thereby a particular angular orientation of the beam elements 130, as shown in FIGS. 23, 24 and 26. The second rotation end housing 180B and the associated beam end housing 152 may also include a second coupling aperture 199B that is at least partially aligned with the axis of the coupling cap screw 154 captured therein and the second coupling aperture 199A of the first rotation end housing 180A when in the particular arrangement, as shown in FIGS. 23, 24 and 26. In this way, when the hinge mechanism 127 is configured/arranged (e.g., the angular orientation of the beam elements 130 is configured/arranged) such that the second coupling aperture 199B at the rotation portion 186 of the first rotation end housing 180A is at least partially aligned with the coupling cap screw 154 associated with the second rotation end housing 180A, FIGS. 23, 24 and 26, a tool may be inserted through the second coupling apertures 199B of the first and second rotation end housings 180A, 180B and the associated beam end housing 152 and into engagement with the coupling cap screw 154 to apply a torque thereto and, ultimately, threadably couple or de-couple the cap screw 154 (and thereby the second rotation end housing 180B and the hinge mechanism 127 as a whole) with the end aperture 132 of a second beam element 130.

It is to be understood that the above description is intended to be illustrative, and not restrictive. Numerous changes and modifications may be made herein by one of ordinary skill in the art without departing from the general spirit and scope of the disclosure as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably connected" is used herein to refer to both connections resulting from separate, distinct components being directly or indirectly coupled and components being integrally formed (i.e., monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the disclosure has been described in detail in connection with only a limited number of embodiments, it should be readily understood that the disclosure is not limited to such disclosed embodiments. Rather, the disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description, but is only limited by the scope of the appended claims.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. An adjustable rail apparatus, comprising:
   an elongate first external fixation beam element comprising a first axis;
   an elongate second external fixation beam element comprising a second axis; and
   a joint coupling the first and second beam elements and configured to selectively adjust the relative angular and rotational arrangement of the first and second beam elements, comprising:
     a first beam end portion comprising a post portion extending from an end portion of the first external fixation beam element;
     a first clamp member axially and rotationally fixed to the post portion of the first beam end portion;
     a first rotation end housing comprising a rotation portion and a post portion coupled with the first clamp member, the first rotation end housing being selectively rotatably adjusted with respect to the first clamp member within a fixed range of rotation;
     a second beam end portion comprising a post portion extending from an end portion of the second external fixation beam element;
     a second clamp member axially and rotationally fixed to the post portion of the second beam end portion; and
     a second rotation end housing comprising a rotation portion and a post portion coupled with the second clamp member, the second rotation end housing being selectively rotatably adjusted with respect to the second clamp member within a fixed range of rotation,
   wherein the rotation portions of the first and second rotation end housings are rotationally fixed and pivotably angularly coupled about a third axis that is angled with respect to the first and second axes of the first and second external fixation beam elements, respectively,
   wherein the first clamp member comprises a first compression screw configured to selectively apply a compressive force to the post portion of the first rotation end housing to selectively rotatably and axially fix the first clamp member and the first rotation end housing, and
   wherein the second clamp member comprises a second compression screw configured to selectively apply a compressive force to the post portion of the second rotation end housing to selectively rotatably and axially fix the second clamp member and the second rotation end housing.

2. The apparatus according to claim 1, wherein the first beam end portion, the first clamp member and the first rotation end housing comprise first apertures that form a first passageway extending from the rotation portion of the first rotation end housing to the end portion of the first external fixation beam element.

3. The apparatus according to claim 1, wherein the first beam end portion, the first clamp member, the first rotation end housing and the second rotation end housing comprise second apertures that form a second passageway extending from the rotation portion of the first rotation end housing to the end portion of the second external fixation beam element in a first relative orientation of the first and second rotation end housings about the axis of rotation.

4. The apparatus according to claim 1, wherein the third axis intersects the first and second axes.

5. The apparatus according to claim 1, wherein the third axis is oriented perpendicular to the first and second axes.

6. The apparatus according to claim 1, wherein the end portion of the first external fixation beam element is positioned within an opening of a sleeve portion of the first beam end portion, and wherein the joint further comprises a first pin member coupled to the sleeve portion and including a portion extending within the opening of the sleeve portion and along a portion of an alignment groove of the first external fixation beam element to rotationally fix the first beam end portion and the first external fixation beam element.

7. The apparatus according to claim 6, wherein the end portion of the first beam element includes an internally threaded axial aperture, wherein the first beam end portion includes an axial aperture extending through the post portion thereof to the opening of the sleeve portion thereof, and wherein the joint further comprises a first screw that comprises an externally threaded shaft portion that is threadably coupled within the internally threaded axial aperture of the end portion of the first beam element to axially fix the first beam element and the first beam end portion.

8. The apparatus according to claim 7, wherein the first screw further comprises a head portion that defines a cross-sectional size that is larger than that of a portion of the axial aperture of the first beam end portion such that the head portion is prevented from axially passing therethrough to axially fix the first beam end portion and the first external fixation beam element.

9. The apparatus according to claim 6, wherein the end portion of the second external fixation beam element is positioned within an opening of a sleeve portion of the second beam end portion, and wherein the joint further comprises a third pin member coupled to the sleeve portion and including a portion extending within the opening of the sleeve portion and along a portion of an alignment groove of the second external fixation beam element to rotationally fix the second beam end portion and the second external fixation beam element.

10. The apparatus according to claim 9, wherein the end portion of the second beam element includes an internally threaded axial aperture, wherein the second beam end portion includes an axial aperture extending through the post portion thereof to the opening of the sleeve portion thereof, and wherein the joint further comprises a second screw that comprises an externally threaded shaft portion that is threadably coupled within the internally threaded axial aperture of the end portion of the second beam element to axially fix the second beam element and the second beam end portion.

11. The apparatus according to claim 10, wherein the second screw further comprises a head portion that defines a cross-sectional size that is larger than that of a portion of the axial aperture of the second beam end portion such that the head portion is prevented from axially passing therethrough to axially fix the second beam end portion and the second external fixation beam element.

12. The apparatus according to claim 11, wherein the second clamp member comprises an internally threaded bore comprising a first end portion that is threadably coupled with the post portion of the second beam end portion and includes a second slot comprising a width that corresponds to a width of the third pin member, and wherein the third pin member further includes a portion extending axially along an outer side of the post portion of the second beam end portion and within the second slot of the threaded bore of the second clamp member to rotationally and axially fix the second clamp member and the second beam end portion.

13. The apparatus according to claim 12, wherein the internally threaded bore of the second clamp member further comprises a second end portion that is threadably coupled with the post portion of the second rotation end housing and includes a second non-threaded recessed portion comprising a width that is wider than a width of a fourth pin member that is coupled to the second rotation end housing, and wherein the fourth pin member includes a portion extending axially along an outer side of the post portion of the second rotation end housing and within the second non-threaded recessed portion of the threaded bore of the second clamp member to selectively allow a limited range of relative rotation between the second clamp member and the second rotation end housing.

14. The apparatus according to claim 13, wherein the second clamp member comprises a compression slot that extends from an outer side thereon to the internally threaded bore along an entire axial length of the second clamp member and a pair of second clamping portions with substantially aligned clamping apertures on opposing sides of the compression slot, and wherein the joint further comprises a second compression screw that extends within the clamping apertures of the second clamping portions and is threadably coupled with at least one of the clamping apertures of the second clamping portions such that rotation of the second clamping screw about an axis thereof in a first direction draws the second clamping portions towards each other and deforms the internally threaded bore of the second clamp member inwardly such that the second clamp member exerts a compressive force on the post portion of the second rotation end housing to selectively rotatably fix the second clamp member and the second rotation end housing, and rotation of the second clamping screw about the axis thereof in a second direction that opposes the first direction allows the internally threaded bore of the second clamp member to deform outwardly such that the second clamp member exerts less compressive force or no compressive force on the post portion of the second rotation end housing to selectively allow the limited range of relative rotation between the second clamp member and the second rotation end housing.

15. The apparatus according to claim 14, wherein the first clamp member comprises an internally threaded bore comprising a first end portion that is threadably coupled with the post portion of the first beam end portion and includes a first slot comprising a width that corresponds to a width of the first pin member, and wherein the first pin member further includes a portion extending axially along an outer side of the post portion of the first beam end portion and within the first slot of the threaded bore of the first clamp member to rotationally and axially fix the first clamp member and the first beam end portion.

16. The apparatus according to claim 15, wherein the internally threaded bore of the first clamp member further comprises a second end portion that is threadably coupled with the post portion of the first rotation end housing and includes a first non-threaded recessed portion comprising a width that is wider than a width of a second pin member that is coupled to the first rotation end housing, and wherein the second pin member includes a portion extending axially along an outer side of the post portion of the first rotation end housing and within the first non-threaded recessed portion of the threaded bore of the first clamp member to selectively allow a limited range of relative rotation between the first clamp member and the first rotation end housing.

17. The apparatus according to claim 16, wherein the first clamp member comprises a compression slot that extends from an outer side thereon to the internally threaded bore along an entire axial length of the first clamp member and a pair of first clamping portions with substantially aligned clamping apertures on opposing sides of the compression slot, and wherein the joint further comprises a first compression screw that extends within the clamping apertures of the first clamping portions and is threadably coupled with at least one of the clamping apertures of the first clamping portions such that rotation of the first clamping screw about an axis thereof in a first direction draws the first clamping portions towards each other and deforms the internally threaded bore of the first clamp member inwardly such that the first clamp member exerts a compressive force on the post portion of the first rotation end housing to selectively rotatably fix the first clamp member and the first rotation end housing, and rotation of the first clamping screw about the axis thereof in a second direction that opposes the first direction allows the internally threaded bore of the first clamp member to deform outwardly such that the first clamp member exerts less compressive force or no compressive force on the post portion of the first rotation end housing to selectively allow the limited range of relative rotation between the first clamp member and the first rotation end housing.

18. The apparatus according to claim 1, wherein the first clamp member comprises an internally threaded bore comprising a first end portion that is threadably coupled with the post portion of the first beam end portion and includes a first slot comprising a width that corresponds to a width of the first pin member, and wherein the first pin member further includes a portion extending axially along an outer side of the post portion of the first beam end portion and within the first slot of the internally threaded bore of the first clamp member to rotationally and axially fix the first clamp member and the first beam end portion.

19. The apparatus according to claim 18, wherein the internally threaded bore of the first clamp member further comprises a second end portion that is threadably coupled with the post portion of the first rotation end housing and includes a first non-threaded recessed portion comprising a width that is wider than a width of a second pin member that is coupled to the first rotation end housing, and wherein the second pin member includes a portion extending axially along an outer side of the post portion of the first rotation end housing and within the first non-threaded recessed portion of the threaded bore of the first clamp member to selectively allow a limited range of relative rotation between the first clamp member and the first rotation end housing.

20. The apparatus according to claim 19, wherein the first clamp member comprises a compression slot that extends from an outer side thereon to the internally threaded bore along an entire axial length of the first clamp member and a pair of first clamping portions with substantially aligned clamping apertures on opposing sides of the compression slot, and wherein the joint further comprises a first compression screw that extends within the clamping apertures of the first clamping portions and is threadably coupled with at least one of the clamping apertures of the first clamping portions such that rotation of the first clamping screw about an axis thereof in a first direction draws the first clamping portions towards each other and deforms the internally threaded bore of the first clamp member inwardly such that the first clamp member exerts a compressive force on the post portion of the first rotation end housing to selectively rotatably fix the first clamp member and the first rotation end housing, and rotation of the first clamping screw about the axis thereof in a second direction that opposes the first direction allows the internally threaded bore of the first clamp member to deform outwardly such that the first clamp member exerts at least one of a less compressive force or no compressive force on the post portion of the first rotation end housing to selectively allow the limited range of relative rotation between the first clamp member and the first rotation end housing.

21. The apparatus according to claim 20, wherein the rotation portions of the first and second rotation end housings are pivotably coupled via a joint pin that defines the third axis.

22. The apparatus according to claim 21, wherein the rotation portions of the first and second rotation end housings comprise a split flange yoke and a shaft portion that are pivotably coupled via the joint pin, the shaft portion being positioned within the split flange yoke.

23. The apparatus according to claim 1, wherein the rotation portions of the first and second rotation end housings are pivotably coupled via a joint pin that defines the third axis.

24. The apparatus according to claim 23, wherein the rotation portions of the first and second rotation end housings comprise a split flange yoke and a shaft portion that are pivotably coupled via the joint pin, wherein the shaft portion is positioned within the split flange yoke.

25. An external bone and/or tissue fixation system, comprising:
   the adjustable rail apparatus according to claim 1; and
   at least one drivable fixation clamp assembly coupled to one of the first and second first external fixation beam element.

26. The fixation system of claim 25, wherein the at least one drivable fixation clamp assembly is configured to axially translate along the one of the first and second first external fixation beam elements via an axial-extending track portion of the exterior surface thereof.

27. The fixation system of claim 26, wherein the axial-extending track portion comprises an externally threaded or patterned engagement track.

28. The fixation system of claim 25, wherein the at least one drivable fixation clamp assembly is rotationally fixed to one of the first and second first external fixation beam elements via an alignment groove thereof.

29. The fixation system of claim 1, wherein the first beam end portion of the joint and the first external fixation beam element are separate and distinct components that are coupled together.

30. The fixation system of claim 29, wherein the second beam end portion of the joint and the second external fixation beam element are separate and distinct components that are coupled together.

31. The fixation system of claim 30, wherein the first beam end portion of the joint and the first external fixation beam element are axially and rotationally fixed together, and the second beam end portion of the joint and the second external fixation beam element are axially and rotationally fixed together.

* * * * *